(12) United States Patent
Okuda et al.

(10) Patent No.: US 9,511,455 B2
(45) Date of Patent: Dec. 6, 2016

(54) SUBSTRATE INSPECTION DEVICE AND COMPONENT MOUNTING DEVICE

(71) Applicant: CKD Corporation, Aichi (JP)

(72) Inventors: Manabu Okuda, Aichi (JP); Tsuyoshi Ohyama, Aichi (JP); Norihiko Sakaida, Aichi (JP)

(73) Assignee: CKD Corporation, Aichi (JP)

(*) Notice: Subject to any disclaimer, the term of this patent is extended or adjusted under 35 U.S.C. 154(b) by 72 days.

(21) Appl. No.: 14/624,124

(22) Filed: Feb. 17, 2015

(65) Prior Publication Data
US 2015/0231744 A1 Aug. 20, 2015

(30) Foreign Application Priority Data

Feb. 17, 2014 (JP) .................. 2014-027386

(51) Int. Cl.
G01N 21/01 (2006.01)
B23K 37/04 (2006.01)
G01N 21/956 (2006.01)
G01R 31/309 (2006.01)
G01R 31/28 (2006.01)

(52) U.S. Cl.
CPC ............. B23K 37/04 (2013.01); G01N 21/956 (2013.01); G01R 31/309 (2013.01); G01N 2021/95646 (2013.01); G01R 31/2813 (2013.01)

(58) Field of Classification Search
CPC H05K 3/3484; H05K 3/1233; H05K 13/0069; H05K 3/1216; H05K 3/1225; H05K 13/08; H05K 13/0061; H05K 2203/163; H05K 2201/09736; H05K 2203/1476; H05K 2203/165; H05K 13/04; H05K 13/0413
See application file for complete search history.

(56) References Cited

U.S. PATENT DOCUMENTS

| 2002/0069517 A1* | 6/2002 | Miura | H05K 13/0069 29/743 |
| 2007/0073428 A1* | 3/2007 | Oohashi | H05K 13/08 700/95 |
| 2012/0304876 A1* | 12/2012 | Miyake | B41F 15/0881 101/114 |
| 2014/0201998 A1* | 7/2014 | Yamashita | H05K 13/0061 29/854 |

FOREIGN PATENT DOCUMENTS

| JP | H06-120700 A | 4/1994 |
| JP | H07-58423 A | 3/1995 |

* cited by examiner

*Primary Examiner* — Michael P Stafira
(74) *Attorney, Agent, or Firm* — Osha Liang LLP

(57) ABSTRACT

A substrate inspection device and a component mounting device are provided. The solder inspection device and the component mounting device respectively have substrate support devices that support a rear face of a printed circuit board. The substrate support device includes backup pins that support the rear surface of the printed circuit board, a location determiner that determines locations of the backup pins, and a backup pin locator that places the backup pins at the locations of the backup pins determined by the location determiner. The location determiner determines positions for supporting areas of the rear face of the printed circuit board where an electrode is covered by a resist film and where neither electronic component nor solder is present, as the locations of the backup pins.

16 Claims, 14 Drawing Sheets

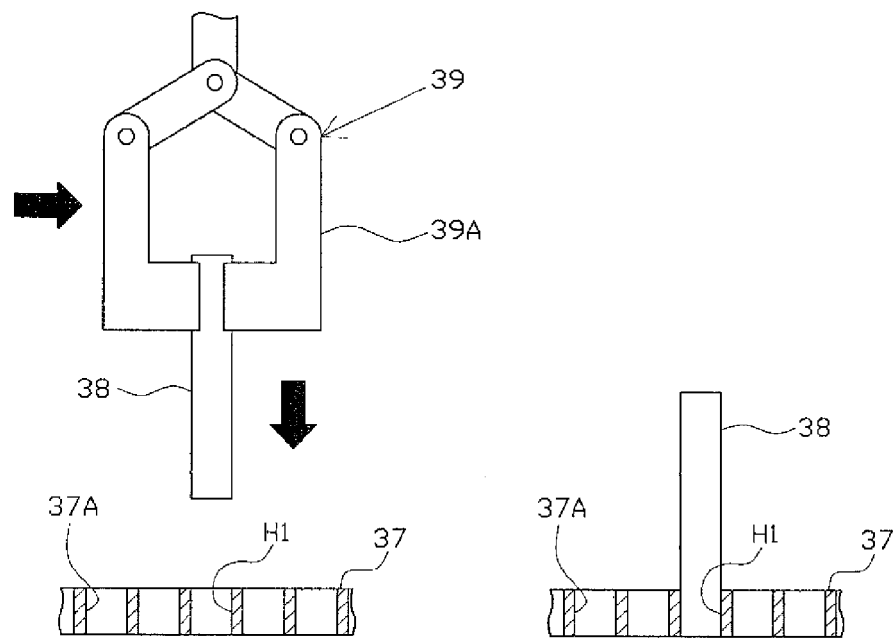
FIG.13 (a)   FIG.13 (b)
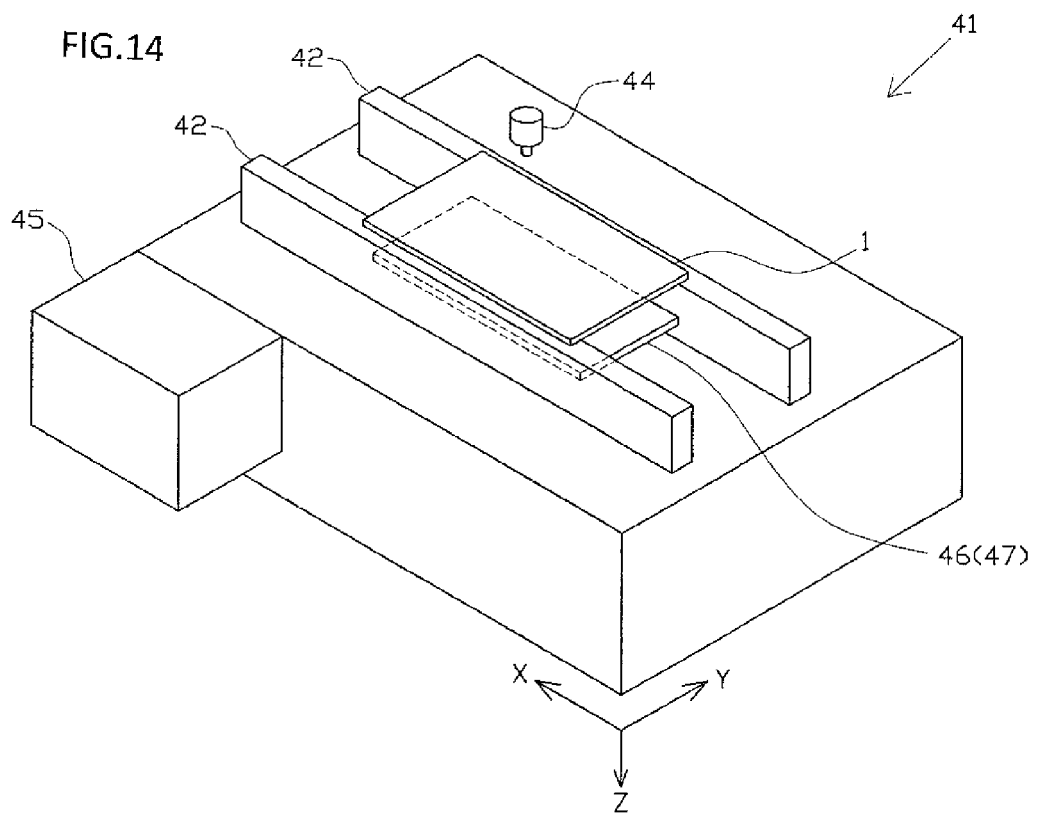

SUBSTRATE INSPECTION DEVICE AND COMPONENT MOUNTING DEVICE

FIELD OF INVENTION

The invention relates generally to a substrate inspection device configured to inspect a substrate, and a component mounting device configured to mount an electronic component on a substrate.

DESCRIPTION OF RELATED ART

A substrate has a base plate made of, for example, a resin and is produced by mounting electrodes (for example, electrode patterns) made of, for example, copper foil, an insulating resist film arranged to cover the electrodes and the base plate, electrically conductive solder paste and electronic components such as ICs and resistances.

In a manufacturing process of the substrate, a solder application device configured to apply solder paste on lands in the electrode patterns for soldering, a component mounting device configured to push and place electronic components into the applied solder paste, and a reflow device configured to fuse the solder paste and connect the electronic components and the electrode patterns are provided along a transfer line of the substrate. In the manufacturing process, an inspection device is also provided to take an image of the substrate and inspect the condition of the applied solder paste and the mounting condition of each component, based on the taken image. Additionally, in the manufacturing process of the substrate, transfer of the substrate, inspection of the substrate and mounting of an electronic component on the substrate are performed in the state that the respective ends of the substrate are supported by two conveyor belts arranged in parallel.

The substrate may have deflection (warp), because of some reason. Inspection of the substrate or mounting of a component in the state that the substrate has deflection may cause and error in the height direction and reduce the accuracy of inspection or may cause a misalignment in location of an electronic component and thereby a mounting failure of the electronic component. In order to suppress deflection of the substrate, a proposed technique supports rear surface of the substrate upward with a plurality of pins (see, for example, JP H06-120700A).

The areas on the rear face of the substrate supported by the backup pins may be any areas where neither electronic components nor lands for soldering are present but where the solder paste, the resist film or the electrodes other than the lands may be present (see, for example, JP H07-58423A).

The areas on the rear face of the substrate where only the electrodes are present or where only the resist film is present have relatively small projection length (thickness) relative to the base plate of the substrate, while the areas where the electrodes are covered by the resist film have relatively large projection length (thickness) relative to the base plate. Accordingly, supporting the rear face of the substrate with the backup pins without any discrimination of these areas like the above technique may result in formation of a relatively large gap (for example, 20 to 70 µm) between the areas of the relatively small projection length (thickness) and the backup pins.

The substrate is likely to have vibration in the presence of such a relatively large gap. This may cause an error especially in the height direction during inspection and reduce the accuracy of inspection.

During mounting of an electronic component, the substrate is likely to be deflected when the electronic component is pushed. This may cause the electronic component to be insufficiently pushed into the solder paste and may result in insufficient fixation of the electronic component (mounting failure of the electronic component).

Additionally, using suction-type backup pins (sucking the substrate toward the backup pins) can suppress the vibration of the substrate but may cause the substrate to be depressed toward the backup pins. There is accordingly a need to extremely increase the depth of field or the dynamic range in the inspection device, in order to ensure the sufficient accuracy of inspection. This may result in increasing the cost.

SUMMARY

One or more embodiments of the invention provide a substrate inspection device that improves the accuracy of inspection without increasing the cost, as well as a component mounting device that more effectively reduces the likelihood of mounting failure of an electronic component.

The following describes some aspects of the invention according to one or more embodiments.

Aspect 1:

According to one aspect, a substrate inspection device inspects a surface of a substrate in a state that a rear face of the substrate is supported, wherein the substrate comprises an electrode, a resist film that covers a predetermined area of the electrode and solder provided to mount a specified electronic component in a specified position of the electrode. The substrate inspection device comprises a substrate support device that supports the rear face of the substrate. The substrate support device comprises: a plurality of backup pins that supports the rear face of the substrate at upper ends thereof; a location determiner that determines locations of the backup pins; and a backup pin locator that places the backup pins at the locations of the backup pins determined by the location determiner. The location determiner determines positions for supporting areas of the rear face of the substrate where the electrode is covered by the resist film and where neither the electronic component nor the solder is present, as the locations of the backup pins.

One or more embodiments of the substrate inspection device of the above aspect 1 enable areas of the substrate having substantially constant protrusion length (thickness) relative to a base plate to be supported by the backup pins. This effectively prevents formation of a significantly large gap between the backup pins and the substrate, thus effectively suppressing vibration of the substrate. As a result, this improves the accuracy of inspection.

In the application using suction-type backup pins, one or more embodiments of the above aspect 1 prevent the sucked areas of the substrate from being depressed toward the backup pins. There is accordingly no need to extremely increase the depth of field or the dynamic range, in order to ensure the sufficient accuracy of inspection. This suppresses an increase in manufacturing cost.

Aspect 2:

In one or more embodiments of the substrate inspection device described in the above aspect 1, the location determiner may identify the areas of the rear face of the substrate where the electrode is covered by the resist film and where neither the electronic component nor the solder is present, based on data regarding design location areas of the electronic component, the solder, the resist film and the electrode on the rear face of the substrate, and determine the identified areas as the locations of the backup pins.

One or more embodiments of the above aspect 2 identify an area to be supported of the substrate, based on the design data. This enables the backup pins to be placed at the positions for adequately supporting the substrate, while relieving the processing load of the location determiner.

Aspect 3:

In one or more embodiments of the substrate inspection device described in either the above aspect 1 or 2, the location determiner may determine the locations of the backup pins, based on at least one of information regarding a design location area of the solder on the surface of the substrate and information regarding an inspection area on the surface of the substrate.

In order to further improve the accuracy of inspection, vibration may be suppressed especially in the areas of the substrate requiring the more precise inspection (for example, the areas where solder areas are closely packed or the areas where small solder areas are formed) and in inspection target areas of the substrate. Such areas especially requiring suppression of vibration may be identified, based on the information regarding the location area of the solder and the information regarding the inspection area.

One or more embodiments of the substrate inspection device of the above aspect 3 determine the locations of the backup pin, based on at least one of the information regarding the design location area of the solder on the surface of the substrate and the information regarding the inspection area on the surface of the substrate. This enables the backup pins to be placed in a closely packed state in the areas especially requiring suppression of vibration and thus more effectively suppresses vibration of the areas of the substrate especially requiring the high inspection accuracy. As a result, this effectively improves the accuracy of inspection.

Aspect 4:

In one or more embodiments of the substrate inspection device described in the above aspect 3, a plurality of solder areas made of the solder may be provided on the surface of the substrate. The substrate inspection device may further comprise a proximity area identifier that identifies a solder proximity area including an area of the surface of the substrate having a design distance between the solder areas equal to or less than a predetermined value. The location determiner is capable of changing a number of the backup pins per unit area, accompanied with changing the locations of the backup pins. The location determiner may determine the locations of the backup pins, such that a number of the backup pins per unit area for supporting an area of the substrate corresponding to the solder proximity area is greater than a number of the backup pins per unit area for supporting a different area of the substrate other than the solder proximity area.

One or more embodiments of the above aspect 4 place a large number of the backup pins in the areas of the substrate corresponding to the solder proximity areas, i.e., the areas of the substrate requiring the more precise inspection. This further improves the accuracy of inspection.

One or more embodiments of the above aspect 4 also places a relatively small number of the backup pins in the areas of the substrate other than the solder proximity areas. This ensures the further efficient arrangement of the backup pins by the backup pin locator, thus enhancing the productivity.

Aspect 5:

In one or more embodiments of the substrate inspection device described in either the above aspect 3 or 4, a plurality of solder areas made of the solder may be provided on the surface of the substrate. The substrate inspection device may further comprise a high density area identifier that identifies a solder high density area including an area of the surface of the substrate having a design number of the solder areas per unit area equal to or greater than a predetermined number. The location determiner is capable of changing a number of the backup pins per unit area, accompanied with changing the locations of the backup pins. The location determiner may determine the locations of the backup pins, such that a number of the backup pins per unit area for supporting an area of the substrate corresponding to the solder high density area is greater than a number of the backup pins per unit area for supporting a different area of the substrate other than the solder high density area.

One or more embodiments of the above aspect 5 place a large number of the backup pins in the areas of the substrate corresponding to the solder high density areas, i.e., the areas of the substrate requiring the more precise inspection. This further improves the accuracy of inspection.

One or more embodiments of the above aspect 5 also place a relatively small number of the backup pins in the areas of the substrate other than the solder high density areas. This ensures the further efficient arrangement of the backup pins, thus enhancing the productivity.

Aspect 6:

In one or more embodiments of the substrate inspection device described in any one of the above aspects 3 to 5, a plurality of solder areas made of the solder may be provided on the surface of the substrate. The substrate inspection device may further comprise a minimum area identifier that identifies a solder minimum area including the solder area of the surface of the substrate having a design area equal to or less than a predetermined value. The location determiner is capable of changing a number of the backup pins per unit area, accompanied with changing the locations of the backup pins. The location determiner may determine the locations of the backup pins, such that a number of the backup pins per unit area for supporting an area of the substrate corresponding to the solder minimum area is greater than a number of the backup pins per unit area for supporting a different area of the substrate other than the solder minimum area.

One or more embodiments of the above aspect 6 place a large number of the backup pins in the areas of the substrate corresponding to the solder minimum areas, i.e., the areas of the substrate requiring the more precise inspection. This further improves the accuracy of inspection.

One or more embodiments of the above aspect 6 also place a relatively small number of the backup pins in the areas of the substrate where only relatively large areas of the solder are present. This ensures the further efficient arrangement of the backup pins, thus enhancing the productivity.

Aspect 7:

In one or more embodiments of the substrate inspection device described in any one of the above aspects 3 to 6, the location determiner is capable of changing a number of the backup pins per unit area, accompanied with changing the locations of the backup pins. The location determiner may determine the locations of the backup pins, such that a number of the backup pins per unit area for supporting an area of the substrate corresponding to an inspection target area is greater than a number of the backup pins per unit area for supporting a different area of the substrate corresponding to a non-inspection target area.

One or more embodiments of the above aspect 7 place a relatively large number of the backup pins in the inspection target areas of the substrate. This extremely effectively suppresses vibration in the inspection target areas of the substrate and thereby further improves the accuracy of inspection.

One or more embodiments of the above aspect 7 also place a relatively small number of the backup pins in the non-inspection target areas of the substrate. This ensures the further efficient arrangement of the backup pins, thus enhancing the productivity.

Aspect 8:

According to another aspect, a component mounting device pushes and mounts an electronic component on solder provided on a surface of a substrate in a state that a rear face of the substrate is supported, wherein the substrate has an electrode, a resist film that covers a predetermined area of the electrode and the solder provided to mount a specified electronic component in a specified position of the electrode. The component mounting device comprises a substrate support device that supports the rear face of the substrate. The substrate support device comprises: a plurality of backup pins that supports the rear face of the substrate at upper ends thereof; a location determiner that determines locations of the backup pins; and a backup pin locator that places the backup pins at the locations of the backup pins determined by the location determiner. The location determiner determines positions for supporting areas of the rear face of the substrate where the electrode is covered by the resist film and where neither the electronic component nor the solder is present, as the locations of the backup pins.

One or more embodiments of the substrate inspection device of the above aspect 1 enables areas of the substrate having substantially constant protrusion length (thickness) relative to a base plate to be supported by the backup pins. This effectively prevents formation of a significantly large gap between the backup pins and the substrate, thus effectively suppressing deflection of the substrate. This enables the electronic component to be sufficiently pushed into the solder without any difficulty during mounting of the electronic component. This more effectively reduces the likelihood of mounting failure of the electronic component.

Aspect 9:

In one or more embodiments of the component mounting device described in the above aspect 8, the location determiner may identify the areas of the rear face of the substrate where the electrode is covered by the resist film and where neither the electronic component nor the solder is present, based on data regarding design location areas of the electronic component, the solder, the resist film and the electrode on the rear face of the substrate, and determine the identified areas as the locations of the backup pins.

One or more embodiments of the above aspect 9 identify an area to be supported of the substrate, based on the design data. This enables the backup pins to be placed at the positions for adequately supporting the substrate, while relieving the processing load of the location determiner.

Aspect 10:

In one or more embodiments of the component mounting device described in either the above aspect 8 or 9, the location determiner may determine the locations of the backup pins, based on at least one of information regarding the electronic component to be mounted on the surface of the substrate and information regarding a design location area of the solder on the surface of the substrate.

According to one or more embodiments, the "information regarding the electronic component" includes, for example, information regarding the size of each electronic component, the number of terminals of the electronic component, the distance between terminals after mounting and the position of the substrate where the electronic component is mounted (information regarding the mounting position). The terminals of the electronic component are connected with the solder. The size of the electronic component to be mounted, the conditions of the terminals and the mounting position of the electronic component are roughly recognizable, based on the information regarding the arrangement of the solder (including the size and the location area of the solder).

In terms of more effectively reducing the likelihood of mounting failure, a large number of the backup pins may be placed in the areas of the substrate where the electronic components are mounted (mounted areas).

During mounting to the substrate, a large-size electronic component is pressed against the solder with a relatively large force, in order to be securely fixed to the solder. In the case of mounting the large-size electronic component, the mounted area of the electronic component may be supported by a large number of backup pins, in order to suppress the deflection of the substrate more effectively.

Additionally, with regard to an electronic component having a large number of terminals, having terminals arranged in a closely packed state or having relatively small terminals, even a slight deviation of the location of the terminal from a target position may cause a mounting failure. In order to prevent the deviation of the location of the terminal, the terminal locating area likely to cause a mounting failure may be supported by a large number of backup pins and that the substrate is securely kept in the horizontal position.

One or more embodiments of the above aspect 10 determine the locations of the backup pins, based on at least one of the information regarding the electronic component and the information regarding the design location area of the solder. This enables the backup pins to be placed in a closely packed state in the areas especially requiring suppression of deflection. As a result, this enables the electronic component to be placed at the target position with the higher accuracy and thereby more effectively reduces the likelihood of mounting failure.

Aspect 11:

In one or more embodiments of the component mounting device described in the above aspect 10, a plurality of solder areas made of the solder may be provided on the surface of the substrate. The component mounting device may further comprise a proximity area identifier that identifies a solder proximity area including an area of the surface of the substrate having a design distance between the solder areas equal to or less than a predetermined value. The location determiner is capable of changing a number of the backup pins per unit area, accompanied with changing the locations of the backup pins. The location determiner may determine the locations of the backup pins, such that a number of the backup pins per unit area for supporting an area of the substrate corresponding to the solder proximity area is greater than a number of the backup pins per unit area for supporting a different area of the substrate other than the solder proximity area.

One or more embodiments of the above aspect 11 place a large number of the backup pins in the areas of the substrate corresponding to the solder proximity areas, i.e., the areas of the substrate where the terminals are arranged in a closely packed state. This effectively suppresses deflection of the substrate in the areas of the substrate especially requiring suppression of deflection. This more effectively reduces the likelihood of mounting failure.

One or more embodiments of the above aspect 11 place a relatively small number of the backup pins in the areas of the substrate other than the solder proximity areas, i.e., the areas of the substrate where the terminals are arranged at some intervals. This ensures the further efficient arrangement of the backup pins, thus enhancing the productivity.

Aspect 12:

In one or more embodiments of the component mounting device described in either the above aspect 10 or 11, a plurality of solder areas made of the solder may be provided on the surface of the substrate. The component mounting device may further comprise a high density area identifier that identifies a solder high density area including an area of the surface of the substrate having a design number of the solder areas per unit area equal to or greater than a predetermined number. The location determiner is capable of changing a number of the backup pins per unit area, accompanied with changing the locations of the backup pins. The location determiner may determine the locations of the backup pins, such that a number of the backup pins per unit area for supporting an area of the substrate corresponding to the solder high density area is greater than a number of the backup pins per unit area for supporting a different area of the substrate other than the solder high density area.

One or more embodiments of the above aspect 12 place a large number of the backup pins in the areas of the substrate corresponding to the solder high density areas, i.e., the areas of the substrate where a large number of terminals are placed. This effectively suppresses deflection of the substrate in the areas of the substrate especially requiring suppression of deflection. This more effectively reduces the likelihood of mounting failure.

One or more embodiments of the above aspect 12 place a relatively small number of the backup pins in the areas of the substrate other than the solder high density areas, i.e., the areas of the substrate where a relatively small number of terminals are placed. This ensures the further efficient arrangement of the backup pins, thus enhancing the productivity.

Aspect 13:

In one or more embodiments of the component mounting device described in any one of the above aspects 10 to 12, a plurality of solder areas made of the solder may be provided on the surface of the substrate. The component mounting device may further comprise a minimum area identifier that identifies a solder minimum area including the solder area of the surface of the substrate having a design area equal to or less than a predetermined value. The location determiner is capable of changing a number of the backup pins per unit area, accompanied with changing the locations of the backup pins. The location determiner may determine the locations of the backup pins, such that a number of the backup pins per unit area for supporting an area of the substrate corresponding to the solder minimum area is greater than a number of the backup pins per unit area for supporting a different area of the substrate other than the solder minimum area.

One or more embodiments of the above aspect 13 place a large number of the backup pins in the areas of the substrate corresponding to the solder minimum areas, i.e., the areas of the substrate where only relatively small terminals are placed. This effectively suppresses deflection of the substrate in the areas of the substrate especially requiring suppression of deflection. This more effectively reduces the likelihood of mounting failure.

One or more embodiments of the above aspect 13 place a relatively small number of the backup pins in the areas of the substrate other than the solder minimum areas, i.e., the areas of the substrate where only relatively large terminals are placed. This ensures the further efficient arrangement of the backup pins, thus enhancing the productivity.

Aspect 14:

In one or more embodiments of the component mounting device described in any one of the above aspects 10 to 13, the location determiner is capable of changing a number of the backup pins per unit area, accompanied with changing the locations of the backup pins. The location determiner may determine the locations of the backup pins, such that a number of the backup pins per unit area for supporting an area of the substrate corresponding to a mounting area of the electronic component is greater than a number of the backup pins per unit area for supporting a different area of the substrate corresponding to a non-mounting area of the electronic component.

One or more embodiments of the above aspect 14 place a relatively large number of the backup pins in the areas of the substrate where the electronic components are mounted. This more effectively suppresses deflection at the mounting position of the electronic component and thereby more effectively reduces the likelihood of mounting failure.

One or more embodiments of the above aspect 14 place a relatively small number of the backup pins in the areas of the substrate where the electronic components are not mounted. This ensures the further efficient arrangement of the backup pins, thus enhancing the productivity.

BRIEF DESCRIPTION OF DRAWINGS

FIGS. 13(a) and 13(b) are partly broken front views illustrating a holder structure for inserting and placing a backup pin in a supporting hole according to one or more embodiments;

FIG. 14 is a perspective view illustrating the general structure of a component molding device according to one or more embodiments;

DESCRIPTION OF EMBODIMENTS

Figure 1:
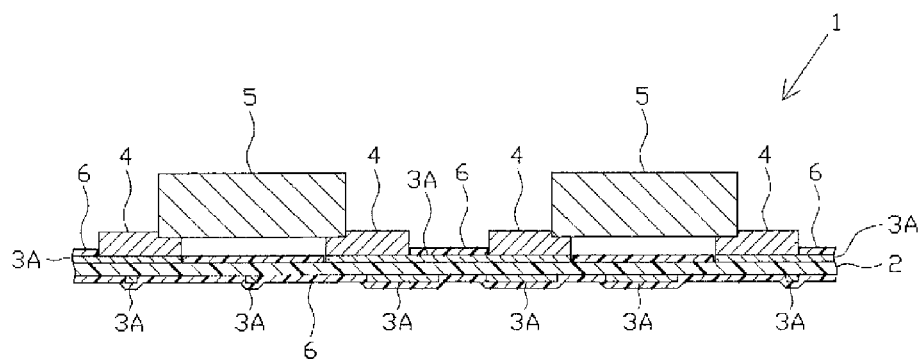
FIG. 1 is an enlarged cross sectional view illustrating the structure of a printed circuit board according to one or more embodiments.

Embodiment of the invention are described below with reference to the drawings. FIG. 1 is an enlarged cross sectional view illustrating part of a printed circuit board 1 as a substrate in a manufacturing process. The printed circuit board 1 includes a base plate 2 and a plurality of electrode patterns 3A made of copper foil and formed on a surface and a rear face of the base plate 2. Solder paste 4 which is viscous solder is printed and formed on the electrode patterns 3A, and electronic components 5 such as IC chips are further mounted on the solder paste 4. More specifically, the electronic component 5 has a plurality of terminals (not shown), each of which is joined with a specified part of the solder paste 4. The printed circuit board 1 also has a translucent resist film 6 formed to cover predetermined areas of the electrode patterns 3A on which the solder paste 4 is not mounted.

Figure 2:
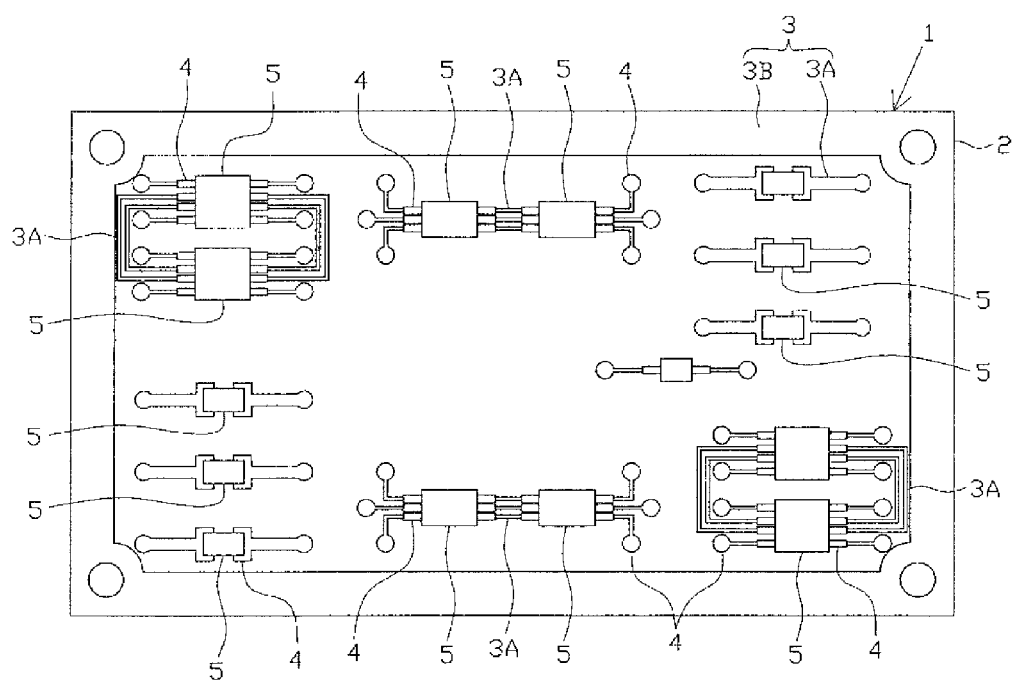
FIG. 2 is a plan view schematically illustrating the structure on a surface of the printed circuit board according to one or more embodiments.
Figure 3:
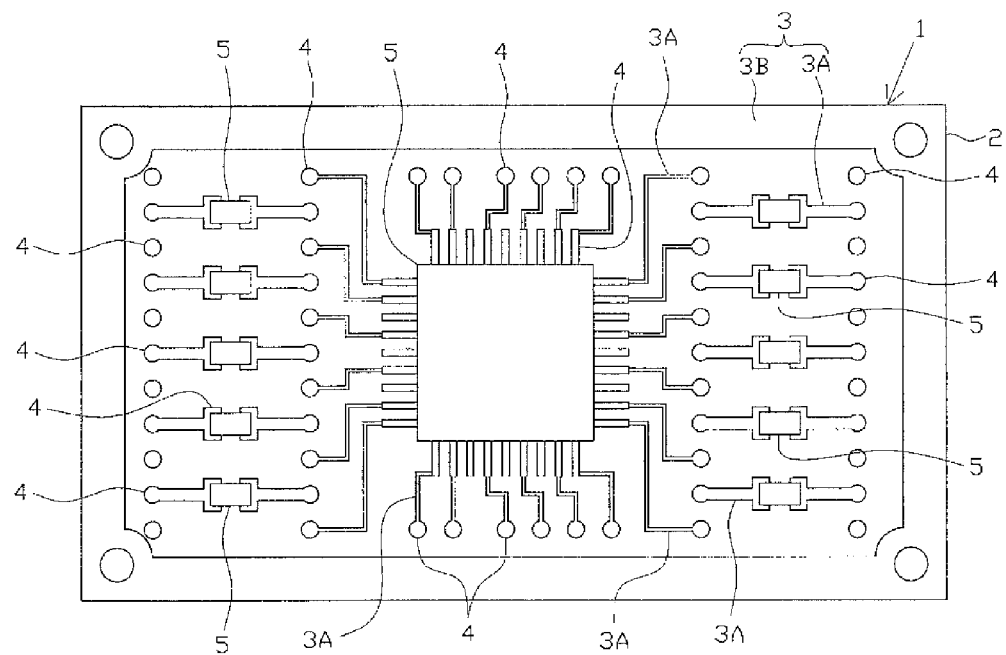
FIG. 3 is a bottom view schematically illustrating the structure on a rear face of the printed circuit board according to one or more embodiments.

As shown in FIGS. 2 and 3 (FIG. 2 shows the surface of the printed circuit board 1 and FIG. 3 shows the rear face of the printed circuit board 1), the printed circuit board 1 of the embodiment is a double-sided mounting substrate on which electronic components 5 are mounted on both the surface and the rear face.

Additionally, a ground electrode 3B is provided on the outer periphery of the printed circuit board 1 to be connected to the ground when the printed circuit board 1 is installed in an object product. According to this embodiment, the electrode patterns 3A and the ground electrode 3B constitute electrodes 3. Specified areas of the electrodes 3 on which the solder paste 4 is not mounted are covered by the resist film 6. The protrusion length (thickness) of the resist film 6 covering the electrodes 3 relative to the base plate 2 is substantially constant at the respective parts of the printed circuit board 1.

Figure 4:
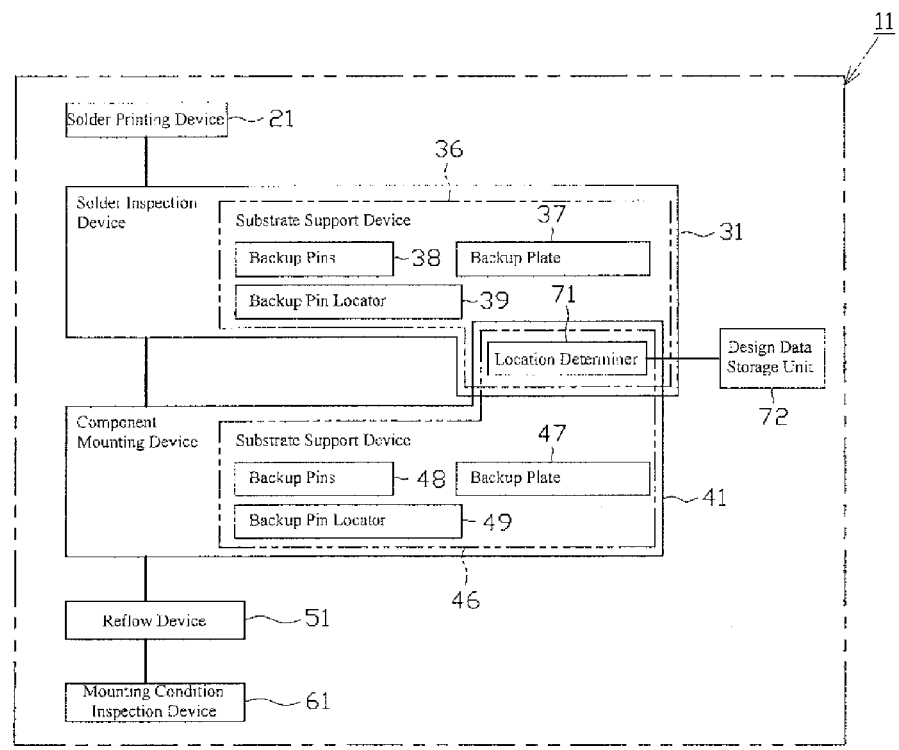
FIG. 4 is a block diagram illustrating the general configuration of a manufacturing system according to one or more embodiments.

The following describes a manufacturing system 11 for manufacturing the printed circuit board 1. As shown in FIG. 4, the manufacturing system 11 of the embodiment includes a solder printing device 21, a solder inspection device 31 as a substrate inspection device, a component mounting device 41, a reflow device 51 and a mounting condition inspection device 61 arranged sequentially from the upstream side (from the upper side in the illustration) along a transfer line of the printed circuit board 1. The manufacturing system 11 of the embodiment supplies the printed circuit board 1 having the electronic components 5 mounted in advance on one face (rear face). In this manufacturing system 11, the other face (surface) of the printed circuit board 1 is subjected to various treatments.

The solder printing device 21 is configured to print and form a predetermined amount of the solder paste 4 in a predetermined area (land) of the electrode pattern 3A. More specifically, the solder printing device 21 has a metal screen (not shown) having a plurality of holes formed at positions corresponding to the lands and uses the metal screen for screen printing of the solder paste 4.

The solder inspection device 31 is configured to inspect the solder paste 4 printed and formed by the solder printing device 21. The component mounting device 41 is configured to push and place the electronic components 5 into the solder paste 4. The solder inspection device 31 and the component mounting device 41 will be described later in detail.

The reflow device 51 is configured to join the electrode patterns 3A with the terminals of the electronic components 5 and fix the electronic components by heating and fusing the solder paste 4.

The mounting condition inspection device 61 inspects, for example, whether the electronic components 5 mounted at predetermined positions and whether electrical continuity with the electronic components 5 is adequately ensured.

Figure 5:
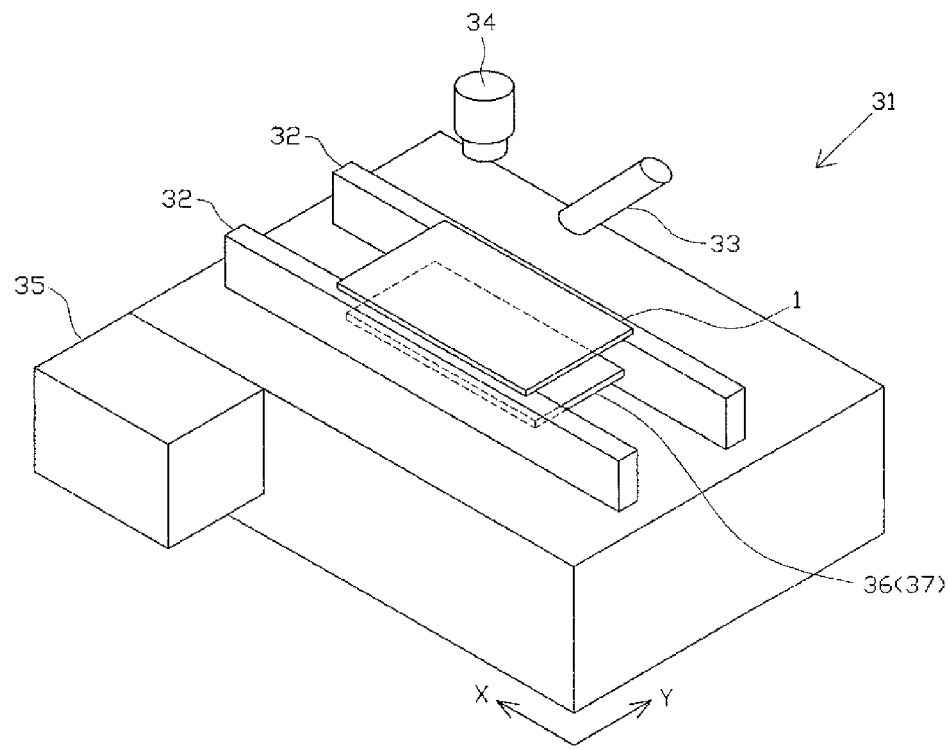
FIG. 5 is a perspective view illustrating the general structure of a solder inspection device according to one or more embodiments.

The configuration of the solder inspection device 31 is described below. As shown in FIG. 5, the solder inspection device 31 includes two conveyor belts 32 arranged in parallel, an irradiation unit 33, an imaging unit 34 (for example, CCD camera), an inspection device control unit 35 and a substrate support device 36.

The conveyor belts 32 are configured to transfer the printed circuit board 1 in the state that the printed circuit board 1 is supported at the both ends thereof. The transfer of the printed circuit board 1 is stopped at a predetermined position by a non-illustrated positioning pin. The solder inspection device 31 inspects the surface of the printed circuit board 1 at a stop.

The irradiation unit 33 irradiates the surface of the printed circuit board 1 obliquely downward with specified light during measurement of the solder paste 4.

The imaging unit 34 is placed immediately above the printed circuit board 1 at a stop to taken an image of an irradiated area on the printed circuit board 1 irradiated with the light. The image data taken by the imaging unit 34 is sent to the inspection device control unit 35. The imaging unit 34 is configured to be movable in the X-axis direction and in the Y-axis direction by a non-illustrated imaging unit drive mechanism and thereby adequately change an imaged area of the printed circuit board 1, i.e., an inspection target area of the printed circuit board 1.

The inspection device control unit 35 performs various controls, image processing and arithmetic operations in the solder inspection device 31. More specifically, the inspection device control unit 35 performs image processing based on the image data sent from the imaging unit 34, so as to measure the area, the height and the volume of the solder paste 4. The inspection device control unit 35 outputs a "printing failure signal" to the component mounting device 41 when, for example, the measured area or height of the solder paste 4 is out of a normal range.

Figure 6:
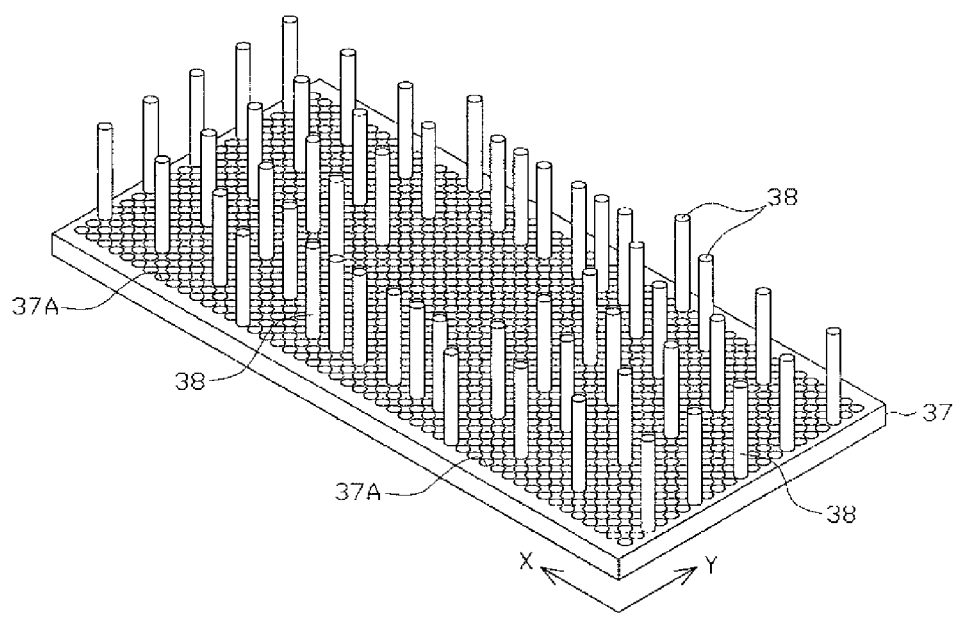
FIG. 6 is a perspective view illustrating a backup plate and backup pins according to one or more embodiments.

The substrate support device 36 supports the printed circuit board 1 upward during inspection. More specifically, the substrate support device 36 includes a backup plate 37 and a plurality of backup pins 38 for supporting the printed circuit board 1 as shown in FIGS. 4 and 6.

The backup plate 37 has a plurality of supporting holes 37A formed at predetermined intervals along both the X-axis direction and the Y-axis direction in a specified metal plate and is placed between the two conveyor belts 32 (see FIG. 5, where the supporting holes 37A and the backup pins 38 are omitted from the illustration of FIG. 5).

The backup pins 38 are in columnar shape and are inserted into the supporting holes 37A to be vertically arranged on the backup plate 37. The backup pins 38 are arranged to support the rear face of the printed circuit board 1 by their upper ends.

An area of the printed circuit board 1 supported by the backup pins 38 (supported area) may be changed by changing the locations of the backup pins 38 on the backup plate 37 (by changing the supporting holes 37A in which the backup pins 38 are inserted). The substrate support device 36 has a location determiner 71 and a backup pin locator 39 to change the locations of the backup pins 38 (i.e., the supported area of the printed circuit board 1). The backup pins 38 are placed on the backup plate 37, prior to the inspection by the solder inspection device 31.

Figure 7:
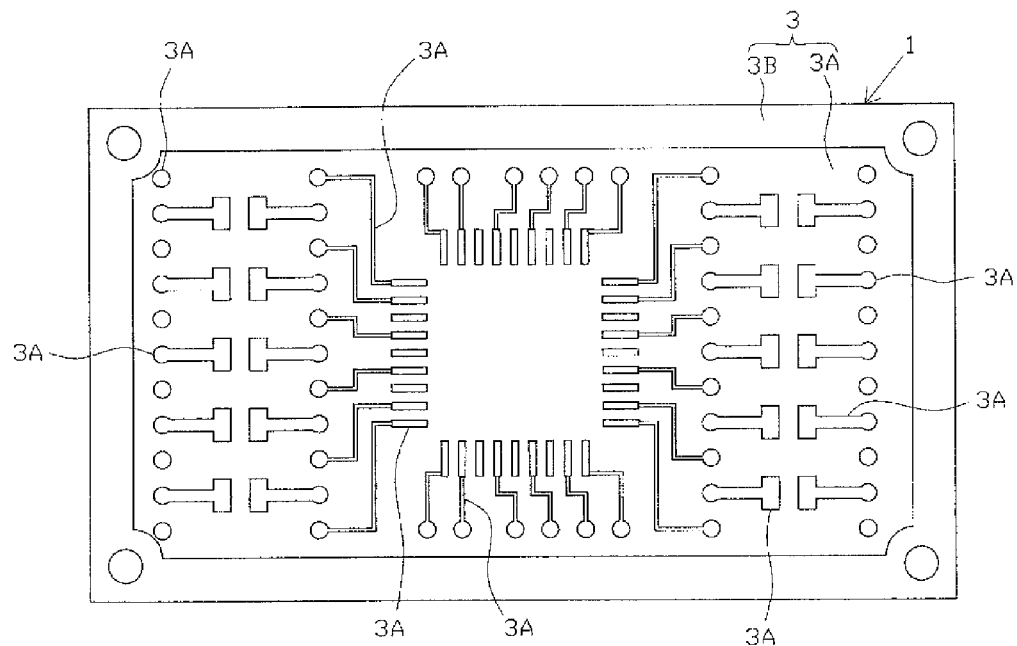
FIG. 7 is a bottom view schematically illustrating the locations of electrodes on the rear face of the printed circuit board according to one or more embodiments.
Figure 8:
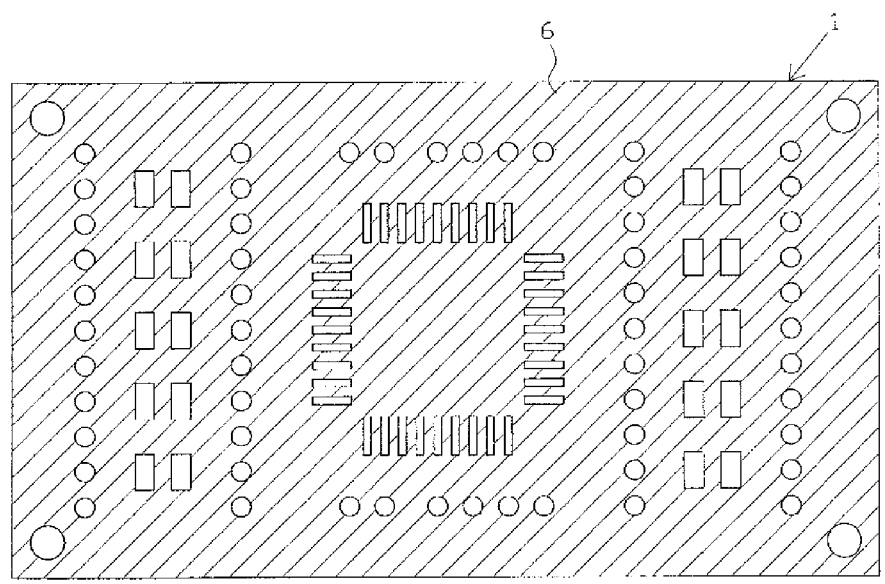
FIG. 8 is a bottom view schematically illustrating the locations of a resist film on the rear face of the printed circuit board according to one or more embodiments.
Figure 9:
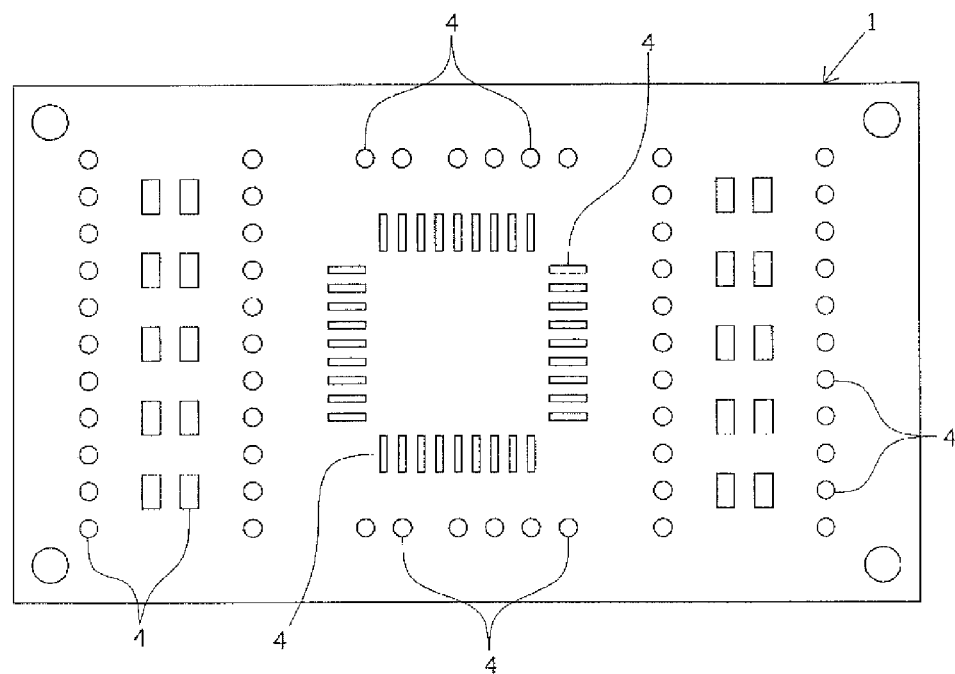
FIG. 9 is a bottom view illustrating the locations of solder paste on the rear surface of the printed circuit board according to one or more embodiments.
Figure 10:
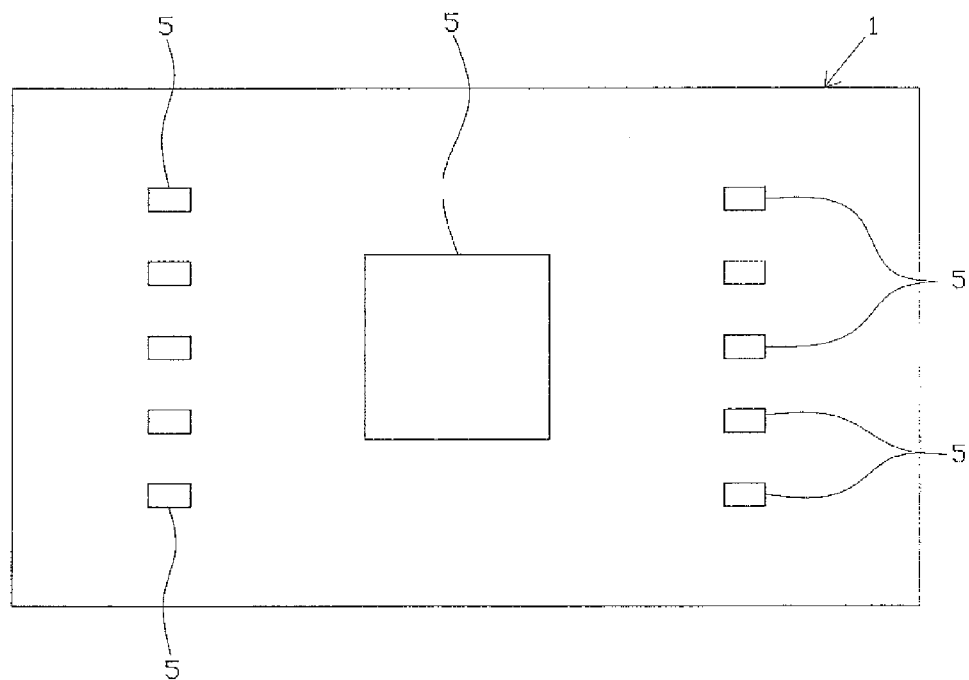
FIG. 10 is a plan view illustrating the locations of electronic components on the rear face of the printed circuit board according to one or more embodiments.

The location determiner 71 is configured to make communication with design data storage unit 72 provided to store design data of the printed circuit board 1. The design data storage unit 72 stores data regarding the areas occupied by the electrodes 3 on the surface and the rear face of the printed circuit board 1 as shown in FIG. 7, data regarding the areas occupied by the resist film 6 (hatched areas in FIG. 8) as shown in FIG. 8, data regarding the areas occupied by the solder paste 4 as shown in FIG. 9 and data regarding the electronic components 5 as shown in FIG. 10 (more specifically, data regarding the mounting positions, the sizes and the shapes of the electronic components 5, the number of terminals and the distance between terminals after mounting). FIGS. 7 to 10 illustrate the relevant structures on the rear face of the printed circuit board 1.

The data regarding the areas occupied by the solder paste 4 and the data regarding the areas occupied by the resist film 6 may be obtained from data on the metal screen used in the solder printing device 21. For example, the areas of the holes in the metal screen correspond to the areas occupied by the solder paste 4, so that the data regarding the areas occupied by the solder paste 4 may be obtained from the data regarding the areas of the holes in the metal screen. The residual areas other than the holes in the metal screen correspond to the areas occupied by the resist film 6, so that the data regarding the areas occupied by the resist film 6 may be obtained from the data regarding the residual areas other than the holes in the metal screen.

The location determiner 71 takes into account the data stored in the design data storage unit 72 and determines the locations of the backup pins 38, based on the data regarding the design areas where the electronic components 5, the solder paste 4, the resist film 6 and the electrodes 3 are located on the rear face of the printed circuit board 1.

Figure 11:
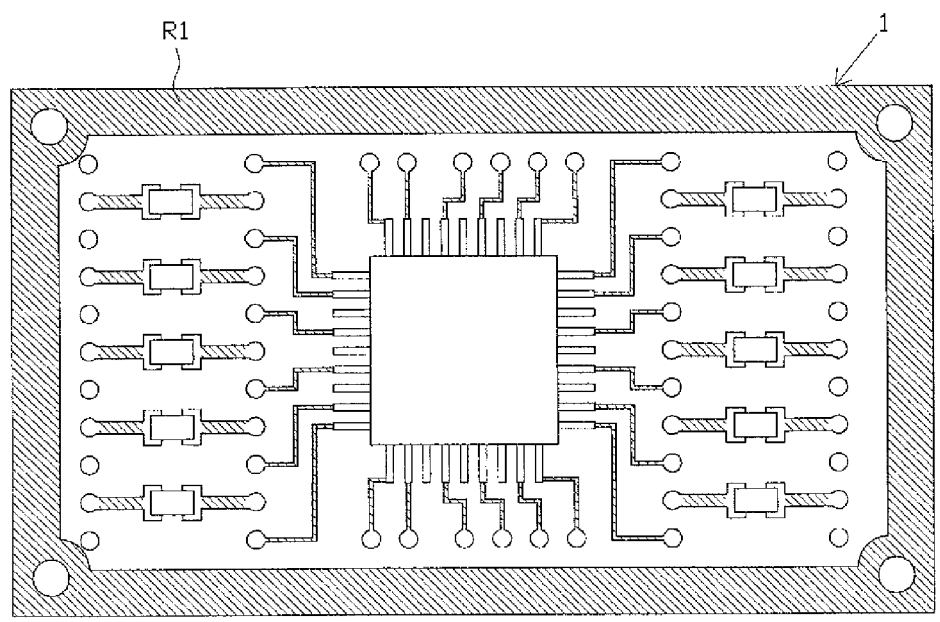
FIG. 11 is a plan view illustrating areas where electrodes are covered by the resist film and where neither electronic components nor solder paste is present according to one or more embodiments.

More specifically, the location determiner 71 identifies overlapped areas of the areas occupied by the electrodes 3 and the areas occupied by the resist film 6, i.e., the areas in which the electrodes 3 are covered by the resist film 6, on the rear face of the printed circuit board 1, based on the data regarding the areas occupied by the electrodes 3 and the data regarding the areas occupied by the resist film 6. The location determiner 71 subsequently excludes the areas on which the electronic components 5 are mounted and the areas in which the solder paste 4 is printed and formed from the identified overlapped areas, based on the data regarding the electronic components 5 and the solder past 4, so as to identify supportable areas R1 (hatched areas in FIG. 11) on the rear face of the printed circuit board 1 as shown in FIG. 11.

Figure 12:
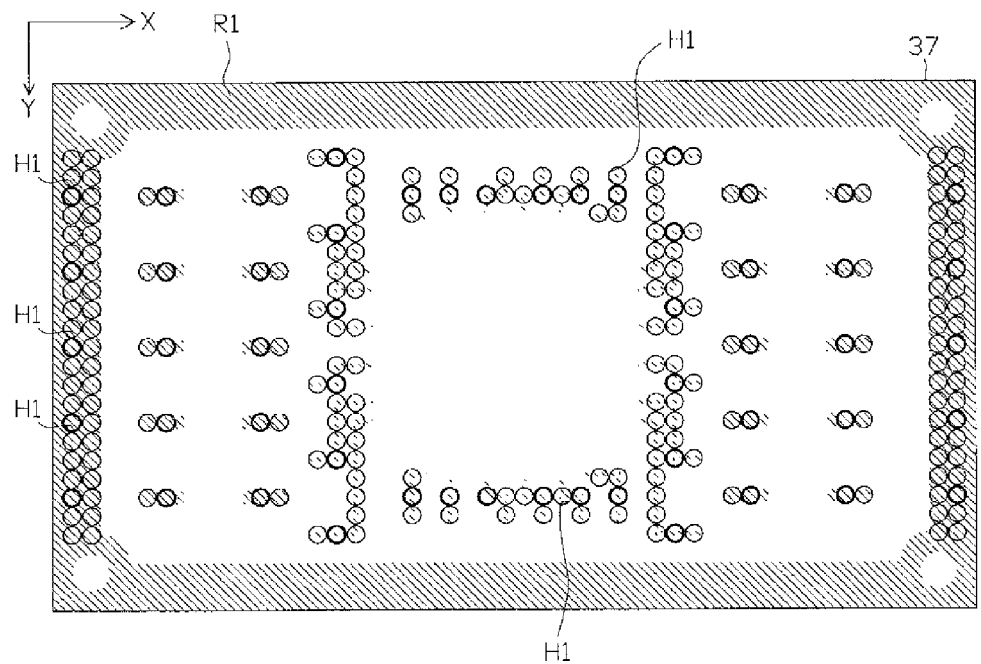
FIG. 12 is a plan view illustrating pin-placeable supporting holes formed in the backup plate according to one or more embodiments.

As shown in FIG. 12, the location determiner 71 then identifies the supporting holes 37A included in the supportable areas R1 and positioned such that the backup pins 38 inserted and placed therein do not interfere with the locations of the electronic components 5 and the solder paste 4, among the supporting holes 37A provided in the backup plate 37, as pin-placeable supporting holes H1 (the supporting holes 37A other than the pin-placeable supporting holes H1 are omitted from the illustration of FIG. 12). The location determiner 71 subsequently determines specified positions of the pin-placeable supporting holes H1 as the locations of the backup pins 38 (in this embodiment, the pin-placeable supporting holes H1 shown by the thick lines in FIG. 12 are determined as the locations of the backup pins 38). In other words, the location determiner 71 identifies the positions for supporting the areas on the rear face of the printed circuit board 1 where the electrodes 3 are covered by the resist film 6 and where neither the electronic components 5 nor the solder paste 4 is present, as the locations of the backup pins 38. Information regarding the determined locations of the backup pins 38 is sent to the inspection device control unit 35.

Any technique may be employed to determine the locations of the backup pins 38 from the plurality of pin-placeable supporting holes H1. For example, one available technique may identify the pin-placeable supporting holes H1 positioned at predetermined row numbers along the X-axis direction and at predetermined column numbers along the Y-axis direction among the supporting holes 37A, as the locations of the backup pins 38.

As shown in FIGS. 13(*a*) and 13(*b*), the backup pin locator 39 includes a holder structure 39A configured to hold each backup pin 38 and a holder structure drive mechanism (not shown) to move the holder structure 39A in all the X-axis direction, the Y-axis direction and the Z-axis direction (height direction).

The backup pin locator 39 is controlled by the inspection device control unit 35 to place the backup pins 38 at the locations of the backup pins 38 determined by the location determiner 71. More specifically, the inspection device control unit 35 controls the holder structure drive mechanism. The holder structure 39A then picks up each backup pin 38 and transfers the backup pin 38 immediately above one of the pin-placeable supporting holes H1 determined as the locations of the backup pins 38. The holder structure 39A then lifts down the backup pin 38 and inserts and places the backup pin 38 in the pin-placeable supporting hole 111. Placing the backup pins 38 in this way enables the areas on the rear face of the printed circuit board 1 where the electrodes 3 are covered by the resist film 6 and where neither the electronic components 5 nor the solder paste 4 is present to be supported by the backup pins 38 during inspection of the surface of the printed circuit board 1.

The following describes the component mounting device 41 with reference to FIG. 14. The component mounting device 41 includes two conveyor belts 42 arranged in parallel, a suction head 44, a mounting device control unit 45 and a substrate support device 46.

The conveyor belts 42 have substantially similar configuration to that of the conveyor belts 42 described above and is configured to transfer the printed circuit board 1 in the state that the printed circuit board 1 is supported at the both ends thereof. The transfer of the printed circuit board 1 is stopped at a predetermined position by a non-illustrated positioning pin. The component mounting device 41 mounts the electronic components 5 on the surface of the printed circuit board 1 at a stop.

The suction head 44 picks up each electronic component 5 and mounts the electronic component 5 on the printed circuit board 1. The suction head 44 is configured to be freely movable in all the X-axis direction, the Y-axis direction and the Z-axis direction by a non-illustrated head drive mechanism.

The mounting device control unit 45 performs various controls in the component mounting device 41 and operates the suction head 44 based on the image data sent from the camera described above to mount each specified electronic component 5 on a specified area of the solder paste 4. When the "printing failure signal" is output from the solder inspection device 31 to the component mounting device 41, the component mounting device 41 does not mount any electronic components 5 on the printed circuit board 1 which the "printing failure signal" is output for, but conveys the printed circuit board 1 to a non-illustrated defective discharge unit.

The substrate support device 46 supports the printed circuit board 1 upward during mounting of the electronic components 5. The substrate support device 46 has substantially similar configuration to that of the substrate support device 36 in the solder inspection device 31 and includes a backup plate 47 and a plurality of backup pins 48 as shown in FIG. 4. The structures of the backup plate 47 and the backup pins 48 are similar to those of the backup plate 37 and the backup pins 38 in the substrate support device 36.

The substrate support device 46 has the location determiner 71 and a backup pin locator 49 to change the locations of the backup pins 48. The location determiner 71 is shared by the solder inspection device 31 and the component mounting device 41. The backup pins 48 are placed on the backup plate 47, prior to mounting of the electronic components 5 by the component mounting device 41.

The location determiner 71 has the configuration described above with respect to the solder inspection device 31. The location determiner 71 directly uses the information regarding the locations of the backup pins 38 in the solder inspection device 31 to determine the locations of the backup pins 48 in the component mounting device 41.

Figure 15:
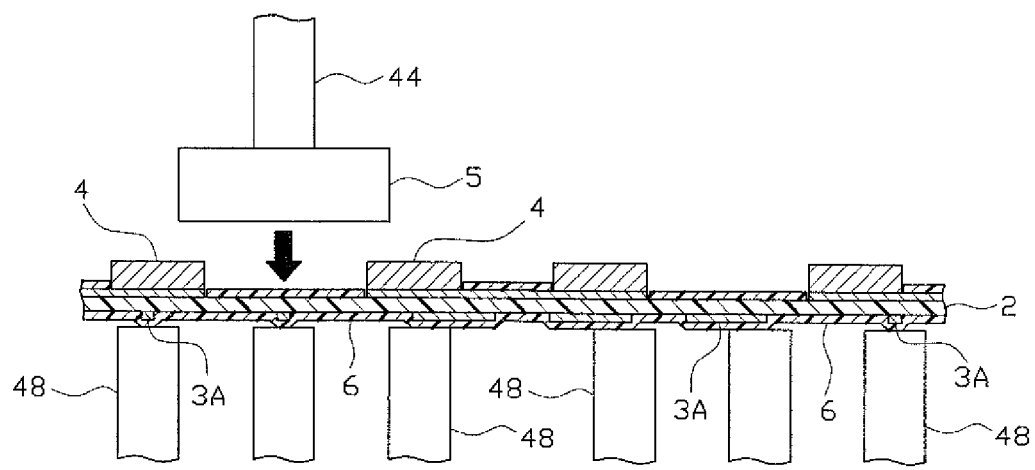
FIGS. 15(a) and 15(b) are partly broken front views illustrating the locations of backup pins during mounting of an electronic component according to one or more embodiments.
Figure 15:
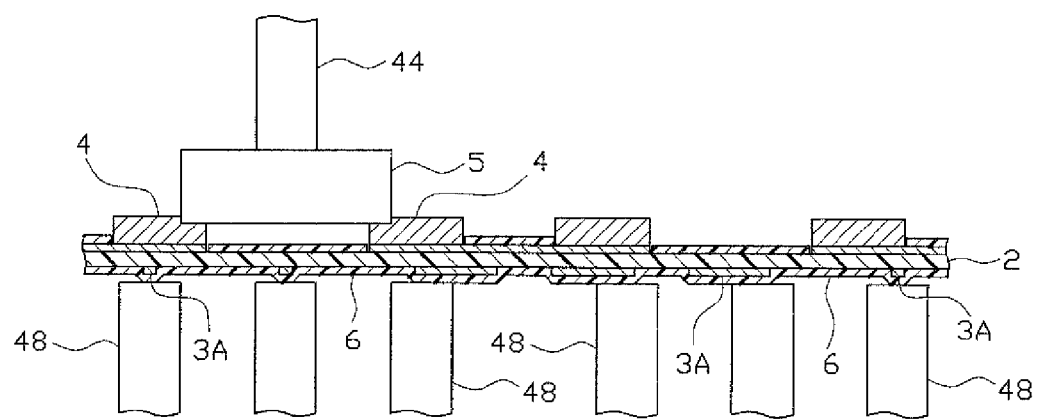

The backup pin locator 49 differs from the backup pin locator 39 by that the backup pin locator 49 is controlled by the mounting device control unit 45, instead of the inspection device control unit 35, but basically has the similar operations to those of the backup pin locator 39. The backup pin locator 49 inserts and places the backup pins 48 into the pin-placeable supporting holes H1 determined as the locations of the backup pins 48. As shown in FIGS. 15(a) and 15(b), placing the backup pins 48 in this way enables the areas on the rear face of the printed circuit board 1 where the electrodes 3 are covered by the resist film 6 and where neither the electronic components 5 nor the solder paste 4 is present to be supported by the backup pins 48 during mounting of the electronic components 5.

As described above, according to this embodiment, the areas of the printed circuit board 1 having the substantially constant protrusion length (thickness) relative to the base plate 2 are supported by the backup pins 38 or 48. This effectively prevents formation of a significantly large gap between the backup pins 38 or 48 and the printed circuit board 1. As a result, this effectively suppresses vibration of the printed circuit board 1 and improves the accuracy of inspection. This also effectively suppresses deflection of the printed circuit board 1 during mounting of the electronic components 5. This enables the electronic components 5 to be sufficiently pushed into the solder paste 4 and more effectively reduces the likelihood of mounting failure of the electronic components 5.

According to this embodiment, the supported area of the printed circuit board 1 is determined, based on the design data stored in advance. This enables the backup pins 38 or 48 to be placed at the positions for adequately supporting the printed circuit board 1, while relieving the processing load of the location determiner 71.

Additionally, the location determiner 71 directly uses the information regarding the locations of the backup pins 38 in the solder inspection device 31 to determine the locations of the backup pins 48 in the component mounting device 41. This further relieves the processing load of the location determiner 71 and improves the efficiency.

The invention is not limited to the above description of the embodiment but may be implemented by any of other aspects described below. There are also various applications and modifications other than those described below.

(a) According to the above embodiment, any technique may be employed to determine the locations of the backup pins 38 or 48 among the plurality of pin-placeable supporting holes H1. According to another embodiment, the locations of the backup pins 38 or 48 may be determined, based on the information regarding design locations of the solder paste 4 on the surface of the printed circuit board 1. In other words, the locations of the backup pins 38 or 48 may be determined according to the state of the surface of the printed circuit board 1.

Figure 16:
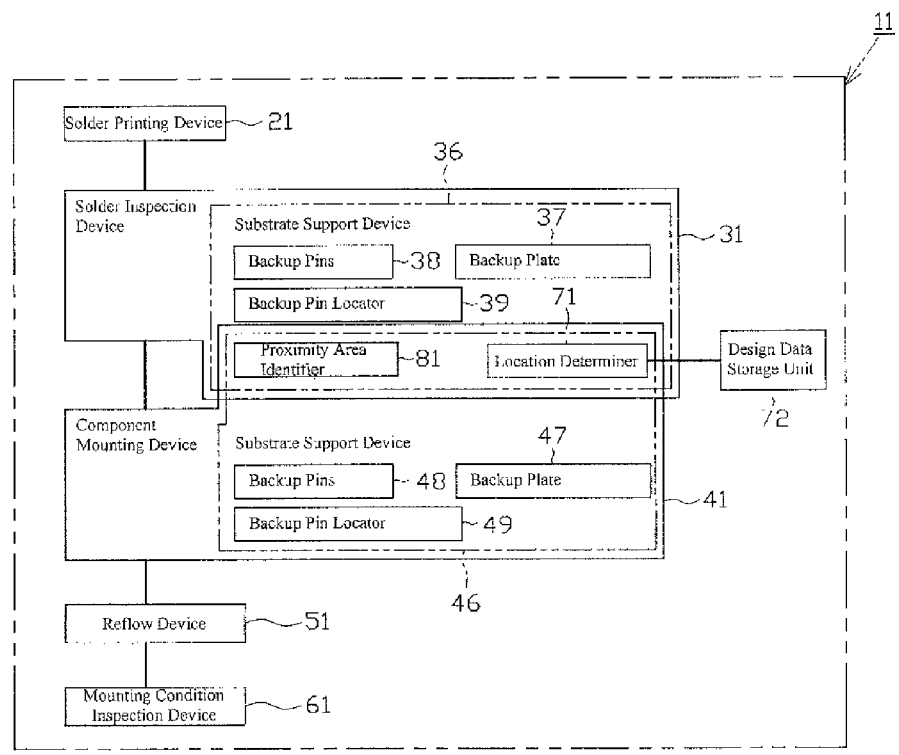
FIG. 16 is a block diagram illustrating the general configuration of a solder inspection device and a component mounting device according to one or more embodiments.
Figure 17:
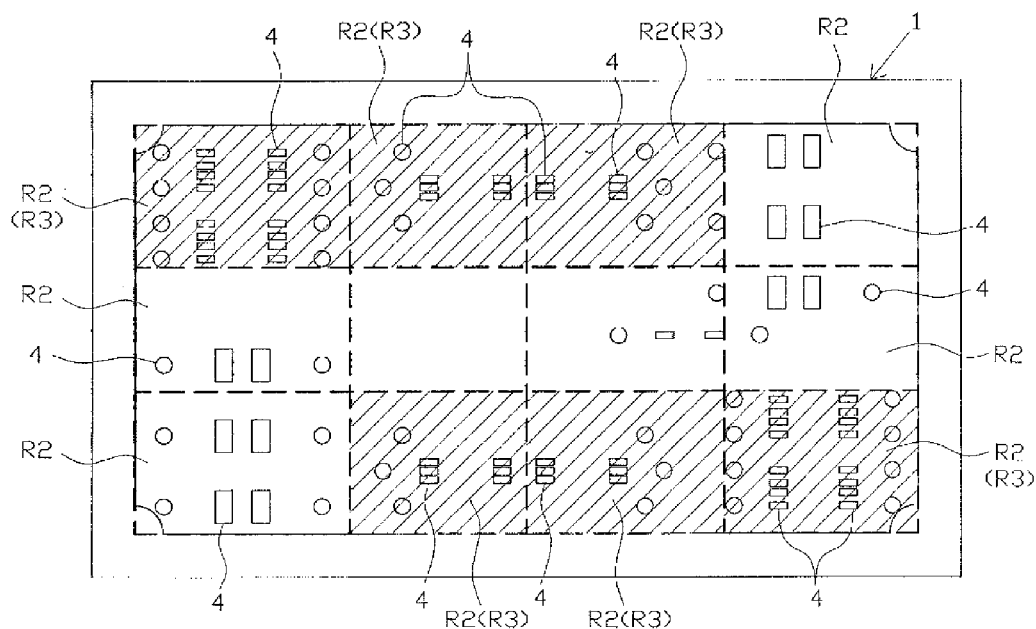
FIG. 17 is a plan view schematically illustrating solder proximity areas according to one or more embodiments.

For example, as shown in FIG. 16, at least one of the solder inspection device 31 and the component mounting device 41 has a proximity area identifier 81 (in this embodiment, the proximity area identifier 81 is shared by the two devices 31 and 41). The proximity area identifier 81 is configured to identify the design distance between the areas of the solder paste 4, based on the data regarding the solder paste 4 stored in the design data storage unit 72. As shown in FIG. 17, the proximity area identifier 81 identifies the design shortest distance between the areas of the solder paste 4 based on the referred data, with respect to each of a plurality of target areas R2 as divisions of the surface area of the printed circuit board 1 (more specifically, the areas where the electronic components 5, the electrode patterns 3A and the solder paste 4 are located). Additionally, the proximity area identifier 81 identifies the target areas R1 including areas having the identified shortest distance equal to or less than a predetermined value, as solder proximity areas R3 (hatched areas in FIG. 17).

Figure 18:
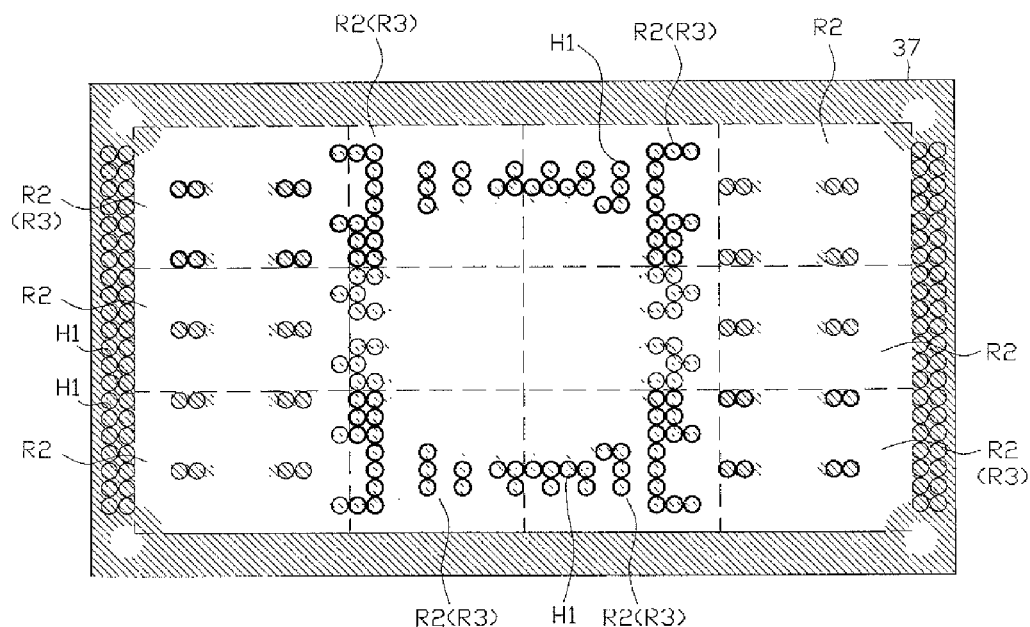
FIG. 18 is a plan view illustrating pin-placeable supporting holes in which a relatively large number of backup pins are placed according to one or more embodiments.

The location determiner 71 then sets the locations of the backup pins 38 or 48, based on the information on the pin-placeable supporting holes H1 and the information on the solder proximity areas R3 identified by the proximity area identifier 81. More specifically, as shown in FIG. 18, the location determiner 71 determines the locations of the backup pins 38 or 48, such that a relatively large number of the backup pins 38 or 48 are placed in the pin-placeable supporting holes H1 included in the solder proximity areas R3 (pin-placeable supporting holes H1 shown by the thick lines in FIG. 18), while a relatively small number of the backup pins 38 or 48 are placed in the pin-placeable supporting holes H1 out of the solder proximity areas R3. In other words, the location determiner 71 determines the locations of the backup pins 38 or 48, such that the number of backup pins 38 or 48 per unit area for supporting the areas of the printed circuit board 1 corresponding to the solder proximity areas R3 is greater than the number of backup pins 38 or 48 per unit area for supporting the residual areas of the printed circuit board 1 other than the solder proximity areas R3. For example, the locations of the backup pins 38 or 48 may be determined, such that the backup pins 38 or 48 are placed in all the pin-placeable supporting holes H1 included in the solder proximity areas R3, while the backup pins 38 or 48 are placed in some of the pin-placeable supporting holes H1 out of the solder proximity areas R3.

In this configuration, the solder inspection device 31 places a large number of the backup pins 38 in the areas of the printed circuit board 1 requiring the more precise inspection. This further improves the accuracy of inspection. The component mounting device 41 effectively suppresses deflection of the printed circuit board 1 especially in the areas of the printed circuit board 1 requiring suppression of deflection. This results in more effectively reducing the likelihood of mounting failure.

A relatively small number of backup pins 38 or 48 are placed, on the other hand, in the areas of the printed circuit board 1 other than the areas corresponding to the solder proximity areas R3. This ensures the further efficient arrangement of the backup pins 38 or 48 by the backup pin locator 39 or 49, thus enhancing the productivity.

Figure 19:
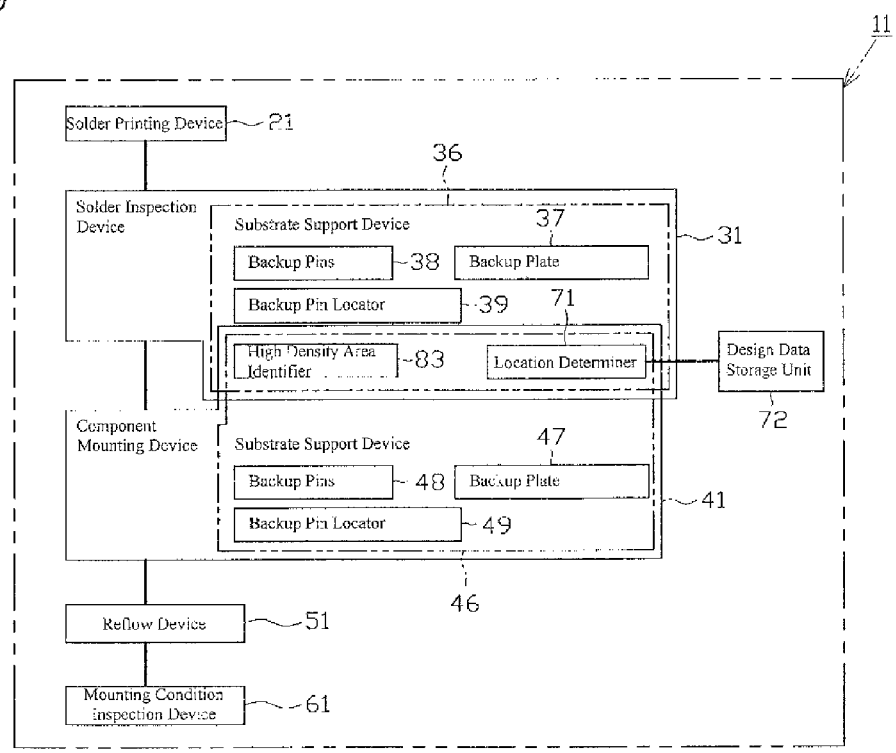
FIG. 19 is a block diagram illustrating the general configuration of a solder inspection device and a component mounting device according to one or more embodiments.
Figure 20:
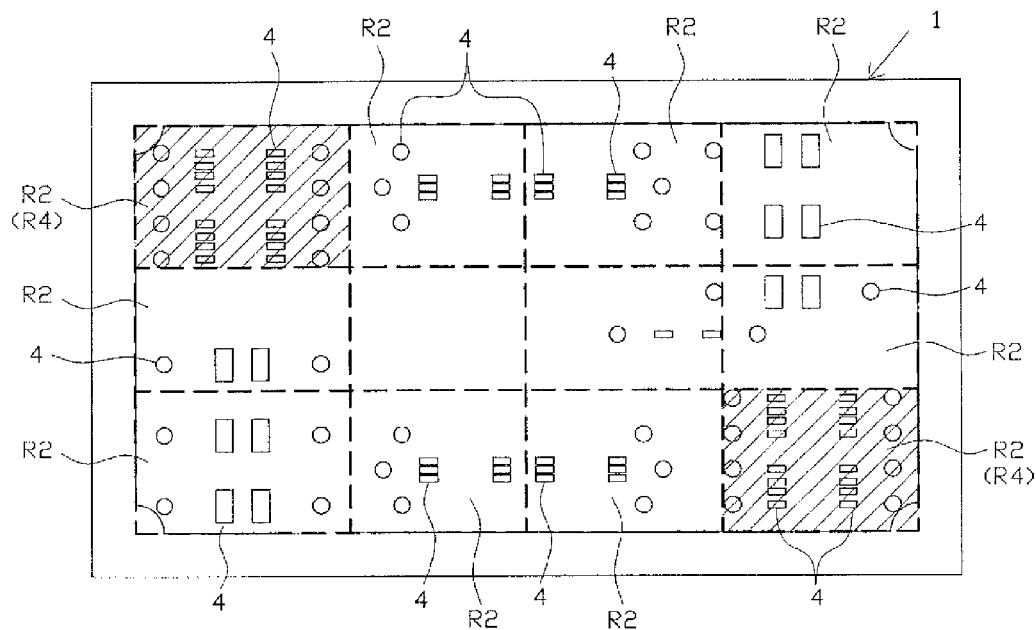
FIG. 20 is a plan view schematically illustrating solder high density areas according to one or more embodiments.

Furthermore, the location determiner 71 may determine the locations of the backup pins 38 or 48, based on the number of the areas of the solder paste 4 per unit area on the surface of the printed circuit board 1. More specifically, as shown in FIG. 19, at least one of the solder inspection device 31 and the component mounting device 41 has a high density area identifier 83 (in this embodiment, the high density area identifier 83 is shared by the two devices 31 and 41). The high density area identifier 83 is configured to identify the design number of the areas of the solder paste 4 per unit area, based on the data regarding the solder paste 4 stored in the design data storage unit 72. Additionally, as shown in FIG. 20, the high density area identifier 83 is configured to identify the target areas R2 including areas having the identified design number of the areas of the solder paste 4 per unit area equal to or greater than a predetermined number, as solder high density areas R4 (hatched areas in FIG. 20).

Figure 21:
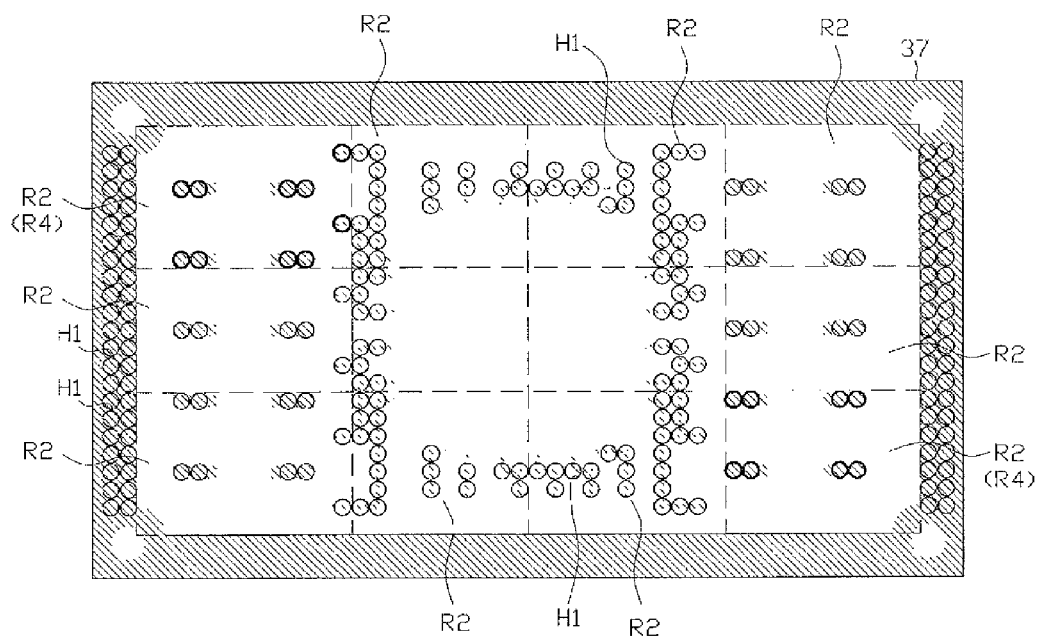
FIG. 21 is a plan view illustrating pin-placeable supporting holes in which a relatively large number of backup pins are placed according to one or more embodiments.

The location determiner 71 then determines the locations of the backup pins 38 or 48, such that a relatively large number of the backup pins 38 or 48 are placed in the pin-placeable supporting holes H1 included in the solder high density areas R4 (pin-placeable supporting holes H1 shown by the thick lines in FIG. 21) identified by the high density area identifier 83, while a relatively small number of the backup pins 38 or 48 are placed in the pin-placeable supporting holes H1 out of the solder high density areas R4. In other words, the location determiner 71 determines the locations of the backup pins 38 or 48, such that the number of backup pins 38 or 48 per unit area for supporting the areas of the printed circuit board 1 corresponding to the solder high density areas R4 is greater than the number of backup pins 38 or 48 per unit area for supporting the residual areas of the printed circuit board 1 other than the solder high density areas R4.

In this configuration, the solder inspection device 31 further improves the accuracy of inspection, and the component mounting device 41 more effectively reduces the likelihood of mounting failure.

Figure 22:
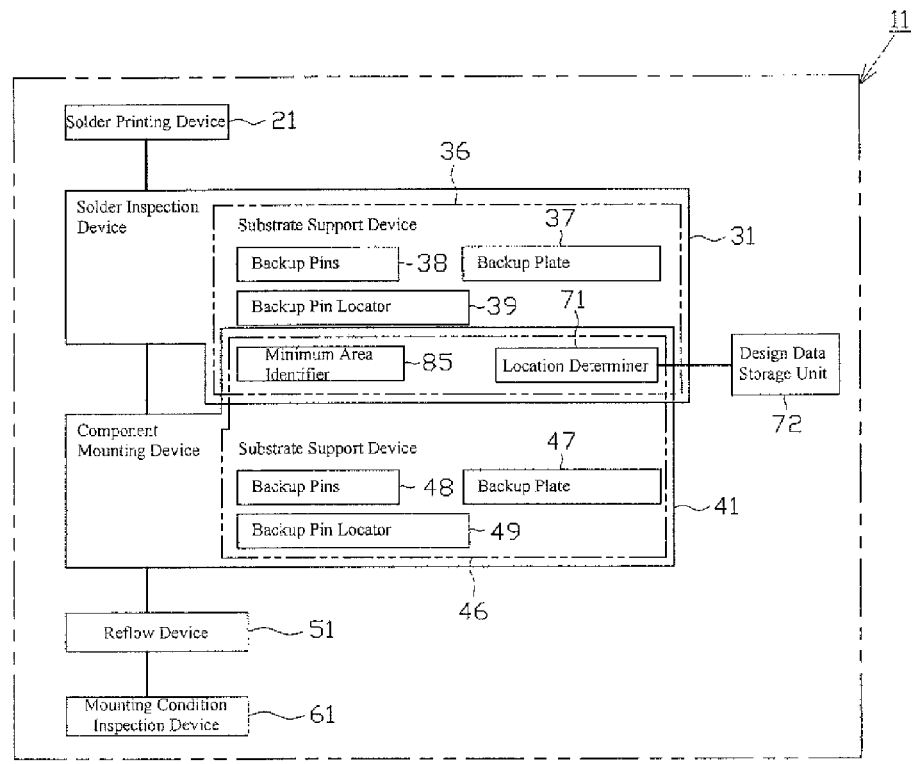
FIG. 22 is a block diagram illustrating the general configuration of a solder inspection device and a component mounting device according to one or more embodiments.
Figure 23:
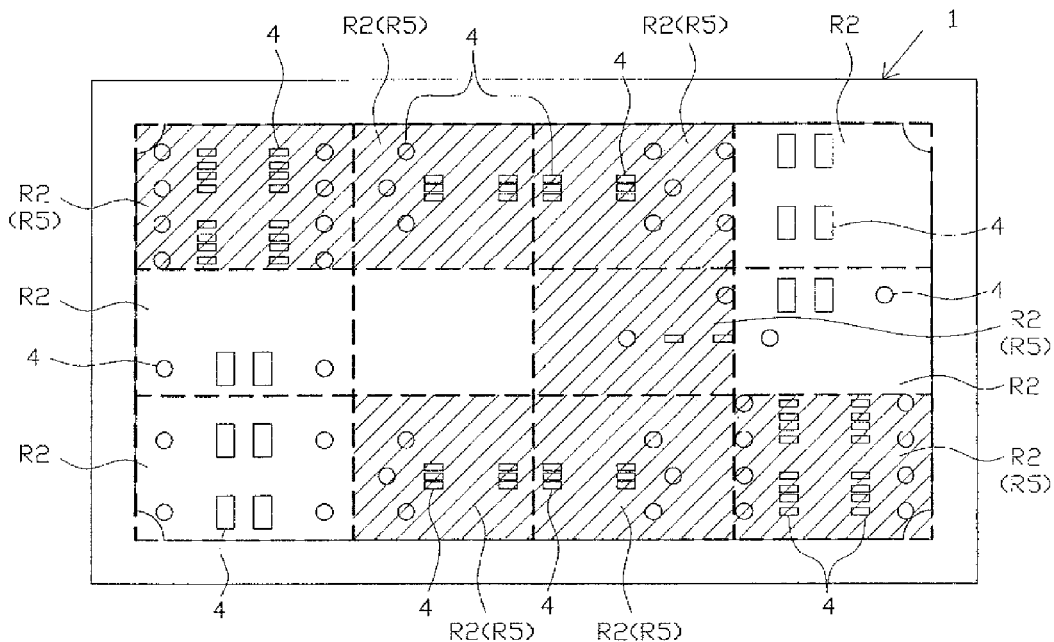
FIG. 23 is a plan view schematically illustrating solder minimum areas according to one or more embodiments.

Furthermore, the location determiner 71 may determine the locations of the backup pins 38 or 48 according to the areas of the solder paste 4 on the surface of the printed circuit board 1. More specifically, as shown in FIG. 22, at least one of the solder inspection device 31 and the component mounting device 41 has a minimum area identifier 85 (in this embodiment, the minimum area identifier 85 is shared by the two devices 31 and 41). The minimum area identifier 85 is configured to identify each design area of the solder paste 4 (each of the areas occupied by the solder paste 4 in an XY plane), based on the data regarding the solder paste 4 stored in the design data storage unit 72. Additionally, as shown in FIG. 23, the minimum area identifier 85 is configured to identify the target areas R2 including areas of the solder paste 4 having the identified design area equal to or less than a predetermined value, as solder minimum areas R5 (hatched areas in FIG. 23).

Figure 24:
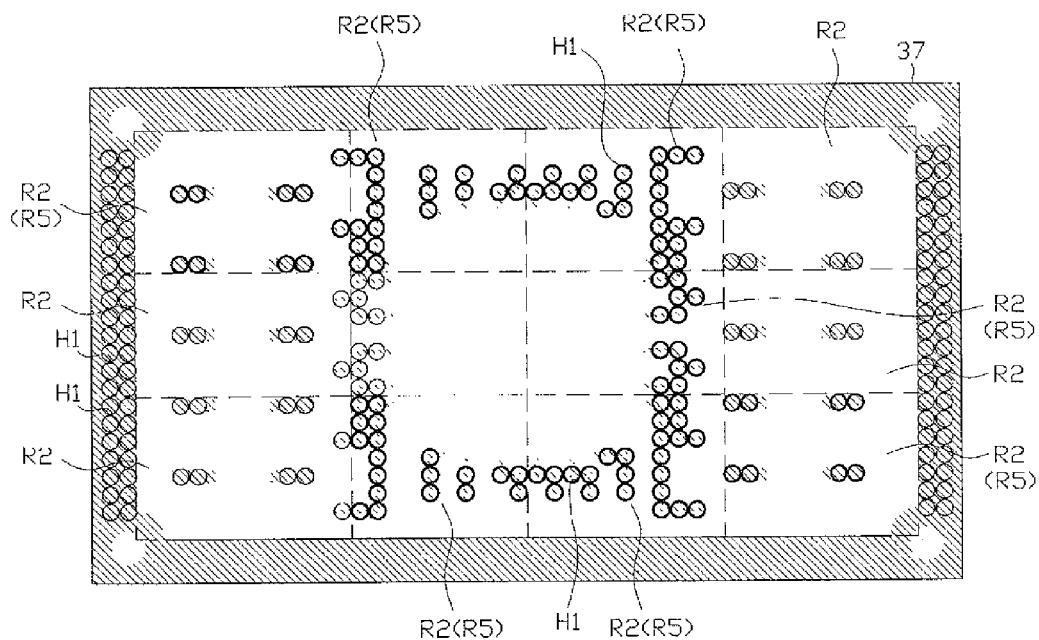
FIG. 24 is a plan view illustrating pin-placeable supporting holes in which a relatively large number of backup pins are placed according to one or more embodiments.

The location determiner 71 then determines the locations of the backup pins 38 or 48, such that a relatively large number of the backup pins 38 or 48 are placed in the pin-placeable supporting holes H1 included in the solder minimum areas R5 (pin-placeable supporting holes H1 shown by the thick lines in FIG. 24) identified by the minimum area identifier 85, while a relatively small number of the backup pins 38 or 48 are placed in the pin-placeable supporting holes H1 out of the solder minimum areas R5. In other words, the location determiner 71 determines the locations of the backup pins 38 or 48, such that the number of backup pins 38 or 48 per unit area for supporting the areas of the printed circuit board 1 corresponding to the solder minimum areas R5 is greater than the number of backup pins 38 or 48 per unit area for supporting the residual areas of the printed circuit board 1 other than the solder minimum areas 115.

In this configuration, the solder inspection device 31 further improves the accuracy of inspection, and the component mounting device 41 more effectively reduces the likelihood of mounting failure.

Figure 25:
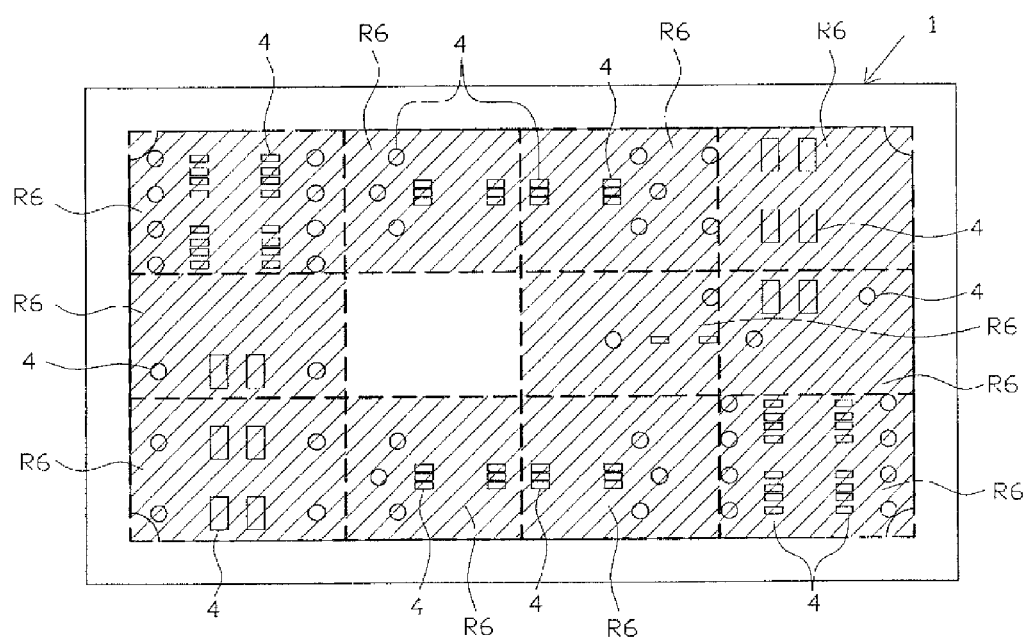
FIG. 25 is a plan view illustrating inspection target areas according to one or more embodiments.

Furthermore, the location determiner 71 in the solder inspection device 31 may determine the locations of the backup pins 38, based on the information regarding the inspection areas on the surface of the printed circuit board 1. For example, data for identifying the inspection areas may be stored in advance in the design data storage unit 72. As shown in FIG. 25, the solder inspection device 31 (for example, the location determiner 71 or the inspection device control unit 35) may be configured to identify inspection target areas R6 (hatched areas in FIG. 25, for example, areas where the solder paste 4 is printed and formed) and non-inspection target areas on the surface of the printed circuit board 1, based on the data regarding the inspection areas stored in advance.

Figure 26:
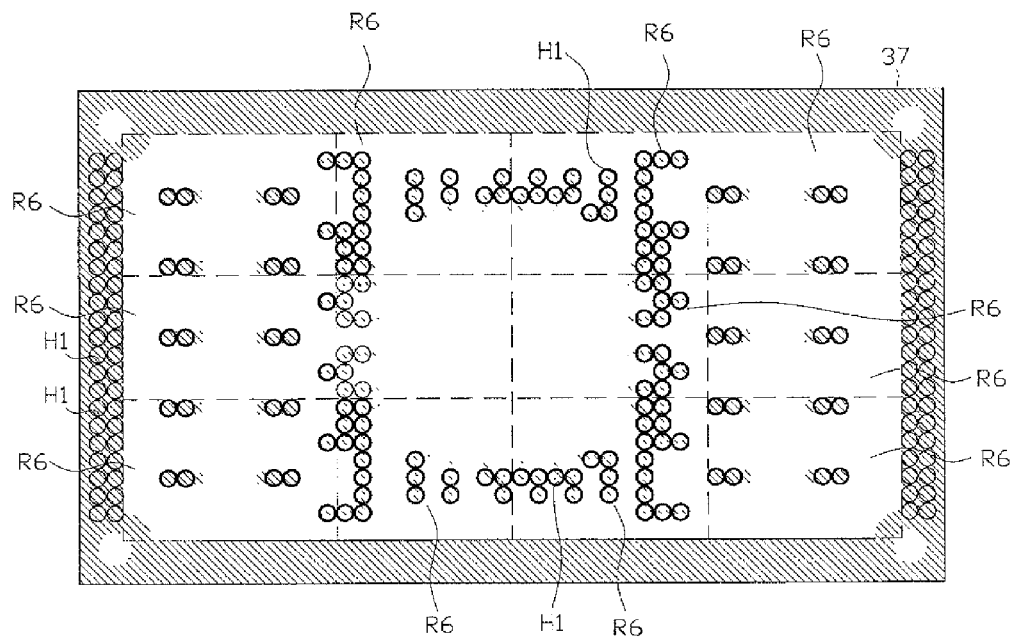
FIG. 26 is a plan view illustrating pin-placeable supporting holes in which a relatively large number of backup pins are placed according to one or more embodiments.

The location determiner 71 then determines the locations of the backup pins 38, such that a relatively large number of the backup pins 38 are placed in the pin-placeable supporting holes H1 included in the inspection target areas R6 (pin-placeable supporting holes H1 shown by the thick lines in FIG. 26), while a relatively small number of the backup pins 38 are placed in the pin-placeable supporting holes H1 included in the non-inspection target areas. In other words, the location determiner 71 determines the locations of the backup pins 38, such that the number of backup pins 38 per unit area for supporting the areas of the printed circuit board 1 corresponding to the inspection target areas R6 is greater than the number of backup pins 38 per unit area for supporting the residual areas of the printed circuit board 1 corresponding to the non-inspection target areas.

This configuration extremely effectively suppresses vibration of the inspection target areas of the printed circuit board 1, thus further improving the accuracy of inspection. A relatively small number of the backup pins 38 are placed in the non-inspection target areas of the printed circuit board 1. This ensures the further efficient arrangement of the backup pins 38, thus enhancing the productivity.

Furthermore, the location determiner 71 in the component mounting device 41 may determine the locations of the backup pins 48, based on the information regarding the electronic components 5 to be mounted on the surface of the printed circuit board 1. For example, the location determiner 71 may take into account the information regarding the size of each electronic component 5, the number of terminals and the mounting position stored in the design data storage unit 72. The location determiner 71 then determines the locations of the backup pins 48, such that a relatively large number of the backup pins 48 are placed in the areas of the printed circuit board 1 where the electronic components 5 are mounted (especially the areas where the large electronic components 5 are mounted), the areas where a number of terminals are provided, the areas where terminals are arranged in a closely packed state and the areas where relatively small terminals are provided, while a relatively small number of the backup pins 48 are placed in the residual areas of the printed circuit board 1.

This configuration enables the backup pins 48 to be placed in a closely packed state in the areas of the printed circuit board 1 especially requiring suppression of deflection. This results in installing the electronic components 5 at the target positions with the higher accuracy, thus more effectively reducing the likelihood of mounting failure.

The size and the number of the target areas R2 are only illustrative and may be changed adequately according to the size and the component density of the printed circuit board 1. Any of the proximity area identifier 81, the high density area identifier 83 and the minimum area identifier 85 may not be shared by the solder inspection device 31 and the component mounting device 41. Each of the devices 31 and 41 may separately have the proximity area identifier 81, the high density area identifier 83 or the minimum area identifier 85.

(b) The above embodiment applies the technical idea of the invention to the solder inspection device 31 and the component mounting device 41. Alternatively the technical idea of the invention may be applied to the mounting condition inspection device 61. According to this modification, the mounting condition inspection device 61 may have a substrate support device configured to cause backup pins of the substrate support device to support the areas on the rear face of the printed circuit board 1 where the electrodes 3 are covered by the resist film 6 and where neither the electronic components 5 nor the solder paste 4 is present.

(c) The printed circuit board 1 is the double-sided mounting substrate in the above embodiment but may be a single-sided mounting substrate. According to this modification, the printed circuit board 1 without mounting the electronic components 5 is supplied to the manufacturing system 11, and the manufacturing system 11 may make one face (surface) of the printed circuit board 1 subjected to various treatments. In this case, neither electronic components 5 nor solder paste 4 is present on the rear face of the printed circuit board 1 supported by the substrate support device 36 or 46.

(d) The structure of the backup pins is not specifically limited but may be a suction type having the function of sucking the printed circuit board 1. In the application using the suction-type backup pins, the configuration of the above embodiment prevents the sucked areas of the printed circuit board 1 from being depressed toward the backup pins 38 or 48. There is accordingly no need to extremely increase the depth of field or the dynamic range, in order to ensure the sufficient accuracy of inspection. This suppresses an increase in manufacturing cost.

Figure 27:
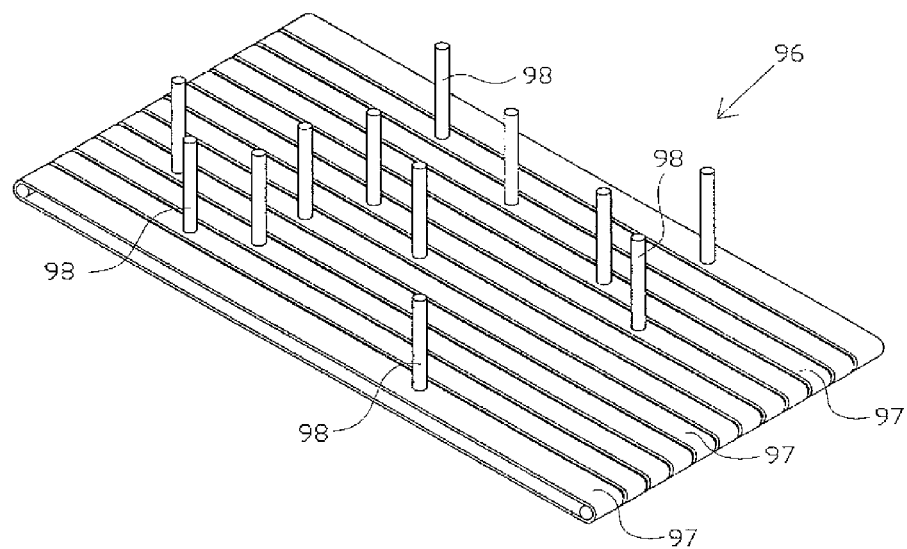
FIG. 27 is a perspective view schematically illustrating the structure of a substrate support device according to one or more embodiments

(e) The substrate support device 36 or 46 of the above embodiment is configured to change the locations of the backup pins 38 or 48 by changing the supporting holes in which the backup pins 38 or 48 are inserted and placed. As shown in FIG. 27, a substrate support device 96 may be configured to have a plurality of conveyor belts 97 arranged in parallel and backup pins 98, each backup pin (or a plurality of backup pins) being vertically arranged on each of the conveyor belts 97. The locations of the backup pins 98 may be changed by rotating and operating the conveyor belts 97.

(f) In the above embodiment, the location determiner 71 is shared by the solder inspection device 31 and the component mounting device 41. Alternatively each of the devices 31 and 41 may separately have the location determiner 71.

(g) Although the above embodiment does not specifically refer to, a pre-reflow mounting condition inspection device may be provided between the component mounting device 41 and the reflow device 51 to inspect the mounting conditions of the electronic components 5, prior to reflow. The technical idea of the invention may be applied to the pre-reflow mounting condition inspection device.

The invention claimed is:

1. A substrate inspection device that inspects a surface of a substrate in a state that a rear face of the substrate is supported, wherein the substrate has an electrode, a resist film that covers a predetermined area of the electrode and solder provided to mount a specified electronic component in a specified position of the electrode, the substrate inspection device comprising a substrate support device that supports the rear face of the substrate, wherein the substrate support device comprises:
a plurality of backup pins that supports the rear face of the substrate at upper ends thereof;
a location determiner that determines locations of the backup pins; and
a backup pin locator that places the backup pins at the locations of the backup pins determined by the location determiner, wherein the location determiner determines positions for supporting areas of the rear face of the substrate where the electrode is covered by the resist film and where neither the electronic component nor the solder is present, as the locations of the backup pins.

2. The substrate inspection device according to claim 1, wherein the location determiner identifies the areas of the rear face of the substrate where the electrode is covered by the resist film and where neither the electronic component nor the solder is present, based on data regarding design location areas of the electronic component, the solder, the resist film and the electrode on the rear face of the substrate, and determines the identified areas as the locations of the backup pins.

3. The substrate inspection device according to claim 1, wherein the location determiner determines the locations of the backup pins, based on at least one of information regarding a design location area of the solder on the surface of the substrate and information regarding an inspection area on the surface of the substrate.

4. The substrate inspection device according to claim 3, wherein a plurality of solder areas made of the solder are provided on the surface of the substrate,
the substrate inspection device further comprising a proximity area identifier that identifies a solder proximity area including an area of the surface of the substrate having a design distance between the solder areas equal to or less than a predetermined value, wherein
the location determiner is capable of changing a number of the backup pins per unit area, accompanied with changing the locations of the backup pins, and
the location determiner determines the locations of the backup pins, such that a number of the backup pins per unit area for supporting an area of the substrate corresponding to the solder proximity area is greater than a number of the backup pins per unit area for supporting a different area of the substrate other than the solder proximity area.

5. The substrate inspection device according to claim 3, wherein a plurality of solder areas made of the solder is provided on the surface of the substrate,
the substrate inspection device further comprising a high density area identifier that identifies a solder high density area including an area of the surface of the substrate having a design number of the solder areas per unit area equal to or greater than a predetermined number, wherein
the location determiner is capable of changing a number of the backup pins per unit area, accompanied with changing the locations of the backup pins, and
the location determiner determines the locations of the backup pins, such that a number of the backup pins per unit area for supporting an area of the substrate corresponding to the solder high density area is greater than a number of the backup pins per unit area for supporting a different area of the substrate other than the solder high density area.

6. The substrate inspection device according to claim 3, wherein a plurality of solder areas made of the solder is provided on the surface of the substrate,
the substrate inspection device further comprising a minimum area identifier that identifies a solder minimum area including the solder area of the surface of the substrate having a design area equal to or less than a predetermined value, wherein the location determiner is capable of changing a number of the backup pins per unit area, accompanied with changing the locations of the backup pins, and
the location determiner determines the locations of the backup pins, such that a number of the backup pins per unit area for supporting an area of the substrate corresponding to the solder minimum area is greater than a number of the backup pins per unit area for supporting a different area of the substrate other than the solder minimum area.

7. The substrate inspection device according to claim 3, wherein the location determiner is capable of changing a number of the backup pins per unit area, accompanied with changing the locations of the backup pins, and
the location determiner determines the locations of the backup pins, such that a number of the backup pins per unit area for supporting an area of the substrate corresponding to an inspection target area is greater than a number of the backup pins per unit area for supporting a different area of the substrate corresponding to a non-inspection target area.

8. A component mounting device that pushes and mounts an electronic component on solder provided on a surface of a substrate in a state that a rear face of the substrate is supported, wherein the substrate has an electrode, a resist film that covers a predetermined area of the electrode and the solder provided to mount a specified electronic component in a specified position of the electrode,
the component mounting device comprising a substrate support device that supports the rear face of the substrate, wherein
the substrate support device comprises:
a plurality of backup pins that supports the rear face of the substrate at upper ends thereof;
a location determiner that determines locations of the backup pins; and
a backup pin locator that places the backup pins at the locations of the backup pins determined by the location determiner, wherein
the location determiner determines positions for supporting areas of the rear face of the substrate where the electrode is covered by the resist film and where neither the electronic component nor the solder is present, as the locations of the backup pins.

9. The component mounting device according to claim 8, wherein the location determiner identifies the areas of the rear face of the substrate where the electrode is covered by the resist film and where neither the electronic component nor the solder is present, based on data regarding design location areas of the electronic component, the solder, the resist film and the electrode on the rear face of the substrate, and determines the identified areas as the locations of the backup pins.

10. The component mounting device according to claim 8, wherein the location determiner determines the locations of the backup pins, based on at least one of information regarding the electronic component to be mounted on the surface of the substrate and information regarding a design location area of the solder on the surface of the substrate.

11. The component mounting device according to claim 10, wherein a plurality of solder areas made of the solder is provided on the surface of the substrate,
the component mounting device further comprising a proximity area identifier that identifies a solder proximity area including an area of the surface of the substrate having a design distance between the solder areas equal to or less than a predetermined value, wherein the location determiner is capable of changing a number of the backup pins per unit area, accompanied with changing the locations of the backup pins, and the location determiner determines the locations of the backup pins, such that a number of the backup pins per unit area for supporting an area of the substrate corresponding to the solder proximity area is greater than a number of the backup pins per unit area for supporting a different area of the substrate other than the solder proximity area.

12. The component mounting device according to claim 10, wherein a plurality of solder areas made of the solder are provided on the surface of the substrate, the component mounting device further comprising a high density area identifier that identifies a solder high density area including an area of the surface of the substrate having a design number of the solder areas per unit area equal to or greater than a predetermined number, wherein the location determiner is capable of changing a number of the backup pins per unit area, accompanied with changing the locations of the backup pins, and the location determiner determines the locations of the backup pins, such that a number of the backup pins per unit area for supporting an area of the substrate corresponding to the solder high density area is greater than a number of the backup pins per unit area for supporting a different area of the substrate other than the solder high density area.

13. The component mounting device according to claim 10, wherein a plurality of solder areas made of the solder is provided on the surface of the substrate, the component mounting device further comprising a minimum area identifier that identifies a solder minimum area including the solder area of the surface of the substrate having a design area equal to or less than a predetermined value, wherein the location determiner is capable of changing a number of the backup pins per unit area, accompanied with changing the locations of the backup pins, and the location determiner determines the locations of the backup pins, such that a number of the backup pins per unit area for supporting an area of the substrate corresponding to the solder minimum area is greater than a number of the backup pins per unit area for supporting a different area of the substrate other than the solder minimum area.

14. The component mounting device according to claim 10, wherein the location determiner is capable of changing a number of the backup pins per unit area, accompanied with changing the locations of the backup pins, and the location determiner determines the locations of the backup pins, such that a number of the backup pins per unit area for supporting an area of the substrate corresponding to a mounting area of the electronic component is greater than a number of the backup pins per unit area for supporting a different area of the substrate corresponding to a non-mounting area of the electronic component.

15. The substrate inspection device according to claim 2, wherein the location determiner determines the locations of the backup pins, based on at least one of information regarding a design location area of the solder on the surface of the substrate and information regarding an inspection area on the surface of the substrate.

16. The component mounting device according to claim 9, wherein the location determiner determines the locations of the backup pins, based on at least one of information regarding the electronic component to be mounted on the surface of the substrate and information regarding a design location area of the solder on the surface of the substrate.

* * * * *